(12) United States Patent
Cinader, Jr.

(10) Patent No.: US 7,653,455 B2
(45) Date of Patent: Jan. 26, 2010

(54) COMPUTER-AIDED IMPLANTING OF ORTHODONTIC ANCHORAGE DEVICES USING SURGICAL GUIDES

(75) Inventor: David K. Cinader, Jr., Yorba Linda, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 384 days.

(21) Appl. No.: 11/460,640

(22) Filed: Jul. 28, 2006

(65) Prior Publication Data

US 2008/0026338 A1   Jan. 31, 2008

(51) Int. Cl.
*G06F 19/00* (2006.01)
*A61C 3/00* (2006.01)

(52) U.S. Cl. .......................... 700/119; 700/118; 433/24
(58) Field of Classification Search .................. 700/95, 700/117–119; 433/24, 29, 72, 75, 133, 215, 433/173; 382/100, 120, 128, 154
See application file for complete search history.

(56) References Cited

U.S. PATENT DOCUMENTS

| | | | | |
|---|---|---|---|---|
| 5,133,660 | A | * | 7/1992 | Fenick ........................ 433/76 |
| 5,320,529 | A | * | 6/1994 | Pompa ........................ 433/76 |
| 5,554,027 | A | * | 9/1996 | Br.ang.nemark ............ 433/172 |
| 5,692,894 | A | * | 12/1997 | Schwartz et al. ............... 433/6 |
| 5,697,779 | A | * | 12/1997 | Sachdeva et al. ............... 433/2 |
| 5,725,376 | A | * | 3/1998 | Poirier ........................ 433/172 |
| 5,800,168 | A | * | 9/1998 | Cascione et al. .............. 433/75 |
| 5,906,488 | A | | 5/1999 | Kvarnstrom |
| 5,921,774 | A | * | 7/1999 | Kanomi et al. ................ 433/18 |
| 5,938,437 | A | * | 8/1999 | DeVincenzo ................. 433/18 |
| 5,967,777 | A | * | 10/1999 | Klein et al. ................... 433/75 |
| 6,068,482 | A | | 5/2000 | Snow |
| 6,382,975 | B1 | * | 5/2002 | Poirier ....................... 433/173 |
| 6,450,812 | B1 | | 9/2002 | Laster et al. |
| 6,547,565 | B1 | | 4/2003 | Dawood et al. |

(Continued)

FOREIGN PATENT DOCUMENTS

DE   19728865   1/1999

(Continued)

OTHER PUBLICATIONS

Curtis M. Becker, David A. Kaiser, Surgical guide for dental implant placement, The Journal of Prosthetic Dentistry, vol. 83, Issue 2, Feb. 2000, pp. 248-251.*

(Continued)

*Primary Examiner*—Albert DeCady
*Assistant Examiner*—Dave Robertson
(74) *Attorney, Agent, or Firm*—Lance L. Vietzke

(57) ABSTRACT

A system for implanting a temporary anchorage device in a jaw bone of a patient makes use of a digital representation of at least a portion of the patient's dental arch, including teeth and corresponding roots, in order to select a temporary anchorage device (TAD) implant site that does not interfere with a tooth root. A surgical guide relates the information from the digital representation to an actual location in the patient's jaw bone. The surgical guide is formed to fit over at least a portion of the occlusal, buccal, labial, and/or lingual surfaces of the dental arch proximate to the selected TAD implant site and includes a physical and/or visual marker that indicates the selected TAD implant site.

35 Claims, 12 Drawing Sheets

U.S. PATENT DOCUMENTS

| | | | |
|---|---|---|---|
| 6,561,805 | B2 | 5/2003 | Kumar |
| 6,655,961 | B2 | 12/2003 | Cottrell |
| 6,788,986 | B1 * | 9/2004 | Traber et al. .................. 700/98 |
| 6,814,575 | B2 * | 11/2004 | Poirier ........................ 433/75 |
| 6,845,175 | B2 | 1/2005 | Kopelman et al. |
| 6,890,174 | B2 | 5/2005 | Kim |
| 6,905,337 | B1 * | 6/2005 | Sachdeva .................... 433/229 |
| 6,923,650 | B2 | 8/2005 | Kurer |
| 7,021,934 | B2 | 4/2006 | Aravena |
| 7,104,795 | B2 * | 9/2006 | Dadi ........................... 433/72 |
| 7,108,511 | B1 | 9/2006 | Shatkin |
| 7,236,842 | B2 * | 6/2007 | Kopelman et al. ............ 700/98 |
| 7,383,094 | B2 * | 6/2008 | Kopelman et al. .......... 700/118 |
| 7,457,443 | B2 * | 11/2008 | Persky ........................ 382/128 |
| 7,474,307 | B2 * | 1/2009 | Chishti et al. ............... 345/418 |
| 7,551,760 | B2 * | 6/2009 | Scharlack et al. ........... 382/128 |
| 7,578,673 | B2 * | 8/2009 | Wen et al. ..................... 433/24 |
| 7,578,674 | B2 * | 8/2009 | Chishti et al. ................. 433/24 |
| 2002/0102517 | A1 * | 8/2002 | Poirier ........................ 433/173 |
| 2003/0215764 | A1 * | 11/2003 | Kopelman et al. ............ 433/24 |
| 2004/0115586 | A1 * | 6/2004 | Andreiko et al. ............... 433/3 |
| 2004/0219471 | A1 | 11/2004 | Cleary et al. |
| 2004/0219473 | A1 | 11/2004 | Cleary et al. |
| 2004/0259051 | A1 * | 12/2004 | Brajnovic .................... 433/75 |
| 2005/0089822 | A1 * | 4/2005 | Geng .......................... 433/215 |
| 2005/0170309 | A1 | 8/2005 | Raby et al. |
| 2005/0170311 | A1 * | 8/2005 | Tardieu et al. ................ 433/76 |
| 2006/0194166 | A1 * | 8/2006 | Jofre Araya .................. 433/72 |
| 2006/0223021 | A1 | 10/2006 | Cinader, Jr. et al. |
| 2008/0085489 | A1 * | 4/2008 | Schmitt ........................ 433/75 |
| 2008/0199827 | A1 * | 8/2008 | Kamer ......................... 433/75 |
| 2009/0042167 | A1 * | 2/2009 | Van Der Zel ................ 433/215 |

FOREIGN PATENT DOCUMENTS

| | | |
|---|---|---|
| WO | WO 03/060825 | 7/2003 |
| WO | WO 2005/034786 | 4/2005 |
| WO | WO 2006/031096 | 3/2006 |
| WO | WO 2008051130 A1 * | 5/2008 |

OTHER PUBLICATIONS

Yen-Chen Ku, Yu-Fu Shen, Fabrication of a radiographic and surgical stent for implants with a vacuum former, The Journal of Prosthetic Dentistry, vol. 83, Issue 2, Feb. 2000, pp. 252-253.*

Fumitaka Takeshita, Tsuneo Suetsugu, Accurate presurgical determination for implant placement by using computerized tomography scan, The Journal of Prosthetic Dentistry, vol. 76, Issue 6, Dec. 1996, pp. 590-591.*

Igor J. Pesun, F. Michael Gardner, Fabrication of a guide for radiographic evaluation and surgical placement of implants, The Journal of Prosthetic Dentistry, vol. 73, Issue 6, Jun. 1995, pp. 548-552.*

Fortin T, Champleboux G, Lormée J, Coudert JL., Precise dental implant placement in bone using surgical guides in conjunction with medical imaging techniques., Journal of Oral Implantology: vol. 26, No. 4, pp. 300-303.*

Stephen M. Parel, R. Gilbert Triplett, Interactive imaging for implant planning, placement, and prosthesis construction, Journal of Oral and Maxillofacial Surgery, vol. 62, Supplement 2, Sep. 2004, pp. 41-47.*

Seong-Hun Kim, Yong-Suk Choi, Eui-Hwan Hwang, Kyu-Rhim Chung, Yoon-Ah Kook, Gerald Nelson, Surgical positioning of orthodontic mini-implants with guides fabricated on models replicated with cone-beam computed tomography, American Journal of Orthodontics and Dentofacial Orthopedics, vol. 131, Issue 4, Supplement 1, Apr. 2007, pp. S82-S89.*

W. De Vos, J. Casselman, G.R.J. Swennen, Cone-beam computerized tomography (CBCT) imaging of the oral and maxillofacial region: A systematic review of the literature, International Journal of Oral and Maxillofacial Surgery, vol. 38, Issue 6, Jun. 2009, pp. 609-625.*

Jason B. Cope, Temporary anchorage devices in orthodontics: A paradigm shift, Seminars in Orthodontics, vol. 11, Issue 1, Temporary Anchorage Devices in Orthodontics, Mar. 2005, pp. 3-9.*

M. Tsuji, N. Noguchi, M. Shigematsu, Y. Yamashita, K. Ihara, M. Shikimori, M. Goto, A new navigation system based on cephalograms and dental casts for oral and maxillofacial surgery, International Journal of Oral and Maxillofacial Surgery, vol. 35, Issue 9, Sep. 2006, pp. 828-836.*

U.S. Appl. No. 11/195,954, filed Aug. 3, 2005.

U.S. Appl. No. 11/275,236, filed Dec. 20, 2005.

Morea et al., "Surgical Guide for Optimal Positioning of Mini-Implants," Journal of Clinical Orthodontics, vol. XXXIX, No. 5, pp. 317-321, 2005.

* cited by examiner

COMPUTER-AIDED IMPLANTING OF ORTHODONTIC ANCHORAGE DEVICES USING SURGICAL GUIDES

TECHNICAL FIELD

The invention relates to orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

An orthodontic anchor, such as a temporary anchorage device (TAD), may be used in combination with a bracket and wire orthodontic system to aid orthodontic tooth movement. A TAD is also referred to as a microimplant or microscrew due to the typical screw-like shape of the device. By acting as a rigid point of support for an orthodontic system, a TAD is useful for achieving forces in a direction not easily obtained with traditional bracket and wire systems. For example, one or more TADS may be surgically implanted in a jaw bone (i.e., the mandible and/or maxilla) of a patient to provide an anchor for a traction element (e.g., a wire or elastic band) that retracts a patient's front teeth inward (i.e., toward the molars). TADs may be used in place of or in addition to head gear, which is a conventional device for aiding orthodontic tooth movement.

In one conventional technique for implanting a TAD, an orthodontic practitioner drills a pilot hole in a patient's jaw bone between the roots of teeth, and subsequently screws the TAD into the pilot hole with a tool such as a small screwdriver or small ratchet wrench. Alternatively, the orthodontic practitioner may utilize a TAD that is self-tapping and does not require a starter hole in order to be implanted in a patient's jaw. A typical TAD is about 4-5 millimeters in length, but the length varies based on a variety of factors, such as the TAD application.

One important consideration when choosing an implant site and orientation of the TAD is the location of the roots of the patient's teeth. For many reasons, it is preferable to avoid perforating a root with the TAD.

SUMMARY

In general, the invention relates to techniques for assisting practitioners in orthodontic diagnosis and treatment. As one example, embodiments of the invention relate to a computer-implemented system and surgical guides that provide guidance to a practitioner during installation of an orthodontic anchorage device, such as a temporary anchorage device (TAD). The system provides a three-dimensional (3D) modeling environment that presents one or more digital representations of a patient's dental arch, including one or more teeth and corresponding roots. By interacting with a modeling environment, a practitioner is able to manipulate a digital representation of the TAD relative to a digital representation of the patient's dental arch in order to locate an appropriate implant site and orientation for the TAD that does not interfere with any of the roots.

The modeling environment allows the practitioner to precisely visualize the location and orientation of the TAD once implanted. In addition, the modeling environment may allow the practitioner to define a variety of parameters that control the implantation of the TAD, including a precise implant location, starting 3D orientation for the TAD, and an insertion depth. The modeling environment may further allow the practitioner to select one or more TADs from a digital library, e.g., database, of industry-standard TADs. In some embodiments, the modeling environment may allow the practitioner to define the insertion path for the TAD, where the path may be non-linear depending upon the particular TAD and the location and arrangement of the patient's teeth.

The surgical guides relate the information from the digital representation to an actual location in the patient's dental arch. That is, the computer-implemented system produces one or more surgical guides based on input provided by the practitioner, e.g., the selected TAD, the implant location, the starting 3D orientation for the TAD, the insertion depth for the TAD and/or the implant path for the TAD. The system produces the surgical guide to include at least one marker that aids the practitioner in implanting the TAD within the patient's dental arch. The marker may be, for example, a physical guide, a visual indicium, an orthodontic appliance that is embedded in the surgical guide or combinations thereof. In one embodiment, the surgical guide includes an alignment surface that is formed in accordance with the 3D modeling environment to fit over (i.e., mate with) at least a portion of an occlusal surface of the patient's dental arch, which helps properly position the surgical guide within the dental arch. Alternatively, the surgical guide may be formed to fit over buccal, labial or lingual surfaces of the teeth of the patient's dental arch.

When forming the surgical guide, the system positions the marker on the surgical guide from data obtained from the digital representation to provide a guide that relates the selected TAD implant site to an actual location in the dental arch of the patient. The marker may be, for example, a marker, an aperture in the surgical guide or a TAD that is embedded in the surgical guide in the desired location. The system may also form the surgical guide so as to assist the practitioner in correctly orienting the TAD during implantation into the jaw bone. In this manner, as described in detail herein, the system may increase the accuracy and precision at which a practitioner may place a TAD, and may decrease the chances of the practitioner inadvertently damaging a tooth root.

In one embodiment, the invention is directed to a system comprising a computing device, modeling software executing on the computing device, and a prototyping instrument. The modeling software comprises a rendering engine that renders a digital representation of at least a portion of a dental arch within a user-interactive computer environment, and a software module that provides a user interface to manipulate a digital representation of a temporary anchorage device relative to the digital representation of the dental arch to specify a virtual implant site for the temporary anchorage device. The prototyping instrument is in communication with the computing device and configured to fabricate an orthodontic surgical guide in accordance with the specified virtual implant site.

In another embodiment, the invention is directed to a surgical guide comprising a body formed to fit over at least one of a buccal, labial, lingual or occlusal surface of at least a portion of a dental arch of a patient, and a marker disposed on the body for indicating a temporary anchorage device implant site, where the marker is positioned on the body by a computer controlled instrument, such as a rapid prototyping instrument or a robotic arm, based on a digital representation of the portion of the dental arch of the patient.

In yet another embodiment, the invention is directed to a method of constructing a guide for implanting a temporary anchorage device. The method comprises generating, within a three-dimensional (3D) modeling environment, a digital representation of a tooth structure of a patient, where the tooth structure includes at least one root location, and receiving input specifying a temporary anchorage device (TAD) implant site within the 3D modeling environment relative to the tooth structure. The method further comprises communicating data relating to the tooth structure of the patient and the specified temporary anchorage device implant site to a prototyping instrument, and controlling the prototyping instrument to fabricate an orthodontic surgical guide having a marker corresponding to the temporary anchorage device implant site.

In another embodiment, the invention is directed to a method comprising generating a digital model of a tooth structure of a patient, selecting a virtual implant site for an orthodontic anchorage device within the digital model of the tooth structure, and fabricating an orthodontic surgical guide based on data from the digital model and virtual implant site. The surgical guide includes a marker positioned to align with an actual implant site for the orthodontic anchorage device corresponding to the virtual implant site when the surgical guide is positioned over the tooth structure of the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
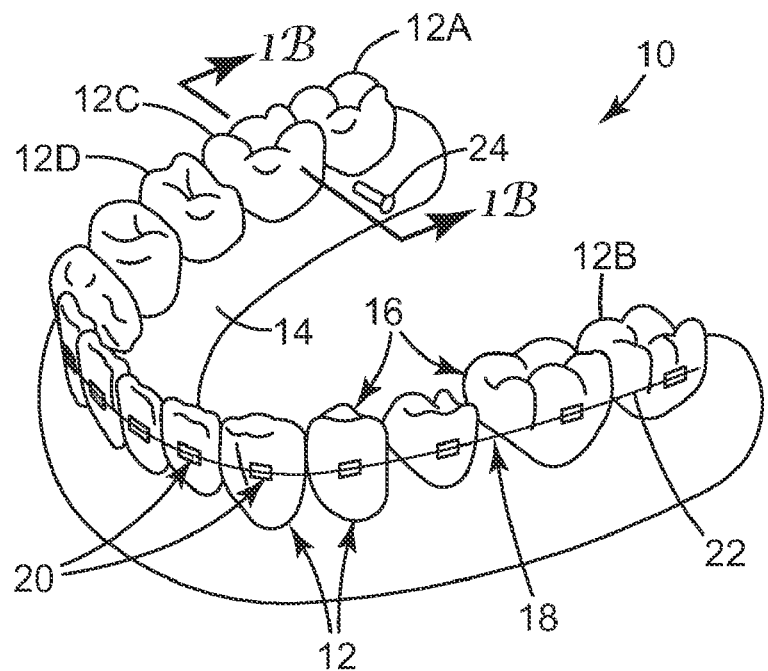
FIG. 1A is a perspective view of a dental arch and an orthodontic system fixed to teeth of the dental arch.

FIG. 1A is a perspective view of dental arch 10. Dental arch 10 is comprised of teeth 12 (which includes individual teeth 12A-12D) supported by jaw bone 14 (schematically shown), which may be a human mandible and/or maxilla. Teeth 12 each include an occlusal surface 16, which generally refers to the outermost tip portions of teeth 12, and a root (shown in FIG. 1B). Occlusal surfaces 16 may also be referred to as occlusal surface 16 of dental arch 10, rather than individual teeth 12, which generally refers to a region that extends along the outermost tip portions of teeth 12.

Fixed to teeth 12 is orthodontic system 18, which includes a plurality of brackets 20 and archwire 22. As known in the art, archwire 22 is received in a slot of each bracket 20 and serves as a track to guide movement of teeth 12 to desired orientations. End sections of archwire 22 are typically received and retained in buccal tubes, one of which is schematically shown in FIG. 1 as attached to molar 12B.

Figure 1B:
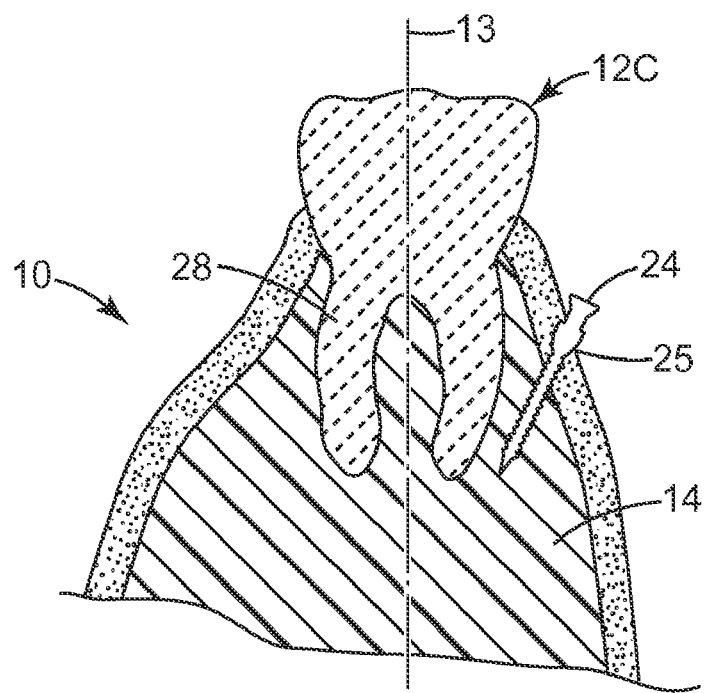
FIG. 1B is a schematic cross-sectional view of a tooth of the dental arch of FIG. 1A taken along line B-B in FIG. 1A, and illustrates a temporary anchorage device implanted in a jaw bone adjacent to a root of the tooth.

As described in further detail below, an orthodontic anchor 24 (shown in FIG. 1B), such as a temporary anchorage device (TAD), may be implanted within dental arch 10 by use of computer-aided placement techniques and a surgical guide formed in an automated fashion. Anchor 24 may be used as a rigid point of connection to archwire 22 or another orthodontic appliance in order to facilitate orthodontic tooth movement. For example, anchor 24 could be coupled to a band that is placed around an adjacent molar tooth. As shown in FIG. 1B, the anchor 24 is typically implanted in jaw bone 14 between roots of teeth 12.

FIG. 1B is a schematic cross-sectional view of tooth 12C of dental arch 10 taken along line B-B in FIG. 1A, and illustrates TAD 24 implanted in jaw bone 14 adjacent to root 28 of tooth 12C. TAD 24 is shown implanted adjacent to tooth 12C for illustrative purposes, and in alternate embodiments, TAD 24 may be implanted in any suitable location in jaw bone. For example, TAD 24 may be implanted adjacent to tooth 12A or tooth 12B (FIG. 1A) of dental arch 10 or another tooth 12, whether it be a molar, premolar, biscuspid, cuspid or incisor. In the embodiment shown in FIG. 1B, TAD 24 is implanted into jaw bone 14 in an oblique direction (about 30 to about 60 degrees) relative to longitudinal direction 13 of tooth 12C. However, in alternate embodiments, the angle of insertion for TAD 24 may be any suitable angle, such as substantially perpendicular to longitudinal direction 13 of tooth 12C, as shown in FIG. 1A. Moreover, as described below, the surgical guide (not shown) may be formed in a computer-assisted manner to substantially aid the practitioner in controlling the location, angle of insertion, and depth of insertion of TAD 24 based on the practitioner's interaction with a 3D modeling environment in which the practitioner manipulates a digital representation of TAD 24 relative to a digital representation of all or a portion of dental arch 10 (FIG. 1A).

TAD 24 may be any surgically implanted orthodontic anchoring device, including, but not limited to, the following examples: TOMAS from Dentaurum of Ispringen, Germany; ORTHO Implant from Imtec Corporation of Ardmore, Okla.; AbsoAnchor from Dentos, Inc. of Daegu City, South Korea; Ortho-Ancho Screw from KLS Martin, L.P. of Jacksonville, Fla.; Aarhus Mini Implant from Medicon eG of Tuttlingen, Germany; RMO Dual Top Anchor System from Rocky Mountain Orthodontics of Denver, Colo.; Leibinger Micro Implant Universal Anchorage System from Stryker Corporation of Portage, Mich.; and Orthodontic Mini Implants from Leone S.p.A. of Firenze Italy. In addition, TAD 24 may be a customized TAD fabricated in an automated or semi-automated manner based on the particular requirements of the patient and, in particular, dental arch 10.

As shown in FIG. 1B, it is often desirable to select TAD implant site 25 in jaw bone 14 such that once implanted, TAD 24 does not interfere with root 28 of tooth 12C. Thus, the practitioner interacts with the 3D modeling environment presented by the computer system to select implant site 25 of TAD 24 and optionally other parameters, such as a starting orientation, an insertion depth and/or an insertion path, so that TAD 24 does not contact root 28 once implanted. Because patient anatomy is typically unique, the location of root 28 of tooth 12C (or other tooth, as the case may be) may differ for every patient. The system described herein provides computer-aided techniques for modeling and locating root 28 of tooth 12C prior to implanting TAD 24, and selecting implant site 25 and other parameters once root 28 is located within the 3D environment. Based on the input from the practitioner or other users, the system forms a patient-specific surgical guide in an automated or semi-automated manner. The surgical guide is formed to be easily and accurately fitted over at least a portion of occlusal surface 16 of tooth 12C (and in some embodiments, over other teeth 12, such as adjacent teeth 12 of dental arch 10) and includes a marker for indicating implant site 25 for TAD 24 once the surgical guide is properly positioned within the patient's mouth. The marker may be formed to visibly mark implant site 25 for TAD 24 and/or the marker may be formed to otherwise align TAD 24 with implant site 25. For example, as discussed below, the surgical guide may include a TAD 24 that has been preembedded in the surgical guide to align with implant site 25 when the surgical guide is properly placed within the patient's mouth. The system may form the surgical structural and/or visual guide in a manner that assists the practitioner in correctly locating and orienting TAD 24 relative to the patient's dental arch 10 during implantation into jaw bone 14.

Figure 2A:
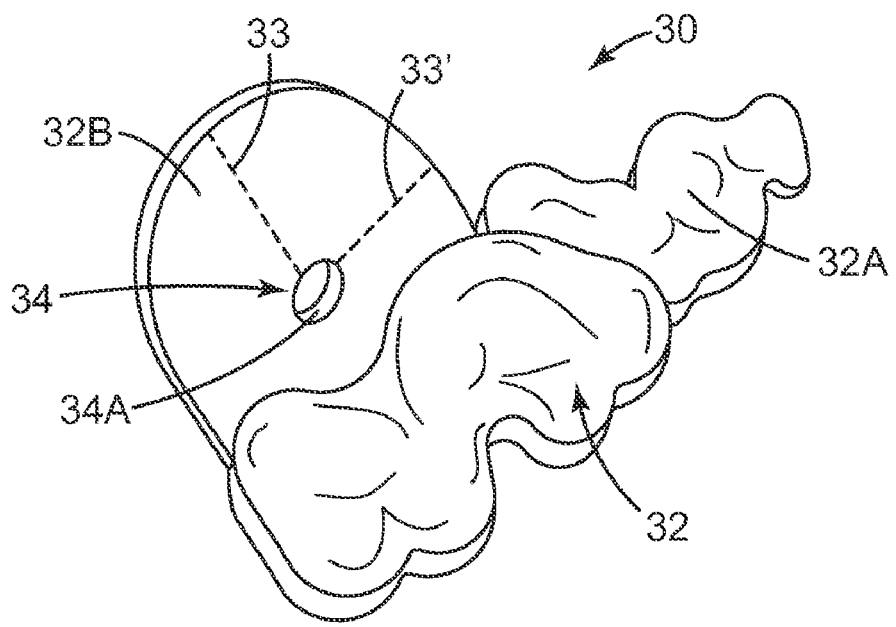
FIG. 2A illustrates an embodiment of a surgical guide in accordance with the invention.

FIG. 2A illustrates an example embodiment of surgical guide 30 in accordance with the invention. In this example, surgical guide 30 includes first body portion 32A and second body portion 32B (collectively referred to as "body 32"). In this example, first and second body portions 32A and 32B, respectively, are integral. In alternate embodiments, first and second body portions 32A and 32B may be separate pieces that are attached together with a suitable attachment means, such as by ultrasonic welding, an adhesive, or a mechanical attachment means (e.g., intermeshing or threaded parts).

First body portion 32A is formed so as to have an alignment surface that accurately positions surgical guide 30 within dental arch 10 and substantially fixes the position of surgical guide 30. For example, the alignment surface of body 32 may be formed in accordance with a digital representation of dental arch 10 so that the alignment surface has a 3D profile that allows surgical guide 30 to fit over at least a portion of occlusal surfaces 16 of teeth 12 of dental arch 10 (shown in FIG. 1A) near the desired TAD implant site 25 (shown in FIG. 1B). In the example embodiment shown in FIG. 2A, the alignment surface is at least partially disposed on first body portion 32A, which is formed and configured to fit over occlusal surfaces 16 of three adjacent teeth 12A, 12C, and 12D. In alternate embodiments, first body portion 32A may be formed to fit over occlusal surfaces 16 of any number of teeth 12, including a single tooth, two teeth, or greater than three teeth, which need not necessarily be adjacent. In some cases, surgical guide 30 exhibits greater integrity and occlusal stability when first body portion 32A fits over an occlusal surface 16 of more than one tooth 12, which may help surgical guide 30 remain in place when a practitioner is implanting TAD 24 in jaw bone 14 (shown in FIG. 1B). In some cases, it may be sufficient for body portion 32A to fit over the buccal, labial, or lingual surfaces of one or more teeth 12.

In this example, second body portion 32B defines aperture 34, which is formed to receive TAD 24. Typically, second body portion 32B is formed to overlay a patient's gums proximate to the desired TAD implant site 25. Once first body portion 32A is properly placed over the occlusal surface 16 of one or more teeth 12, aperture 34 within second body portion 32B aligns with TAD implant site 25 on jaw bone 14 for implanting TAD 24. The position of aperture 34 in second body portion 32B is, as described below, determined based on the practitioner's or other user's review and/or manipulation of a digital representation of TAD 24 relative to a digital representation of dental arch 10 within a 3D modeling environment.

In some embodiments, aperture 34 is also formed to guide TAD 24 into jaw bone 14 (shown in FIG. 1A) at a predetermined angle of insertion. For example, in the embodiment shown in FIG. 2A, inner wall 34A of aperture 34 is formed to receive and support TAD 24 and orient TAD 24 in the correct direction for implantation within jaw bone 14 of the patient. If an oblique TAD 24 angle of insertion is desired as shown in FIG. 1B, inner wall 34A may be also be angled.

Second body portion 32B includes frangible seam 33, which allows surgical guide 30 to be removed from a patient's mouth after TAD 24 is introduced into aperture 34 and implanted in jaw bone 14. Frangible seam 33 enables surgical guide 30 to "break away" around implanted TAD 24. In other embodiments, frangible seam 33 may be placed in any suitable place on body 32. For example, frangible seam 33' indicates another suitable location for frangible seam 33.

Surgical guide 30 may be constructed of any suitable material, including, but not limited to, thermoplastics and thermosets. Preferably, the material used to form surgical guide 30 is capable of being sterilized, such as in an autoclave. Examples of suitable thermoplastic materials include a polyamide nylon, such as a DuraForm brand polyamide nylon available from 3D Systems of Valencia, Calif. or a glass-filled nylon, such as DuraForm brand glass-filled nylon available from 3D Systems. When surgical guide 30 is constructed via a stereolithography rapid prototyping instrument, suitable stereolithography resins include: Somos brand stereolithography materials available from DSM of Heerlen, the Netherlands, Fototec brand stereolithography materials available from Dreve Otoplastik GmbH of Unna, Germany, and Accura brand stereolithography materials available from 3D Systems. Somos brand stereolithography materials include resins reinforced with glass or ceramic.

Figure 13:
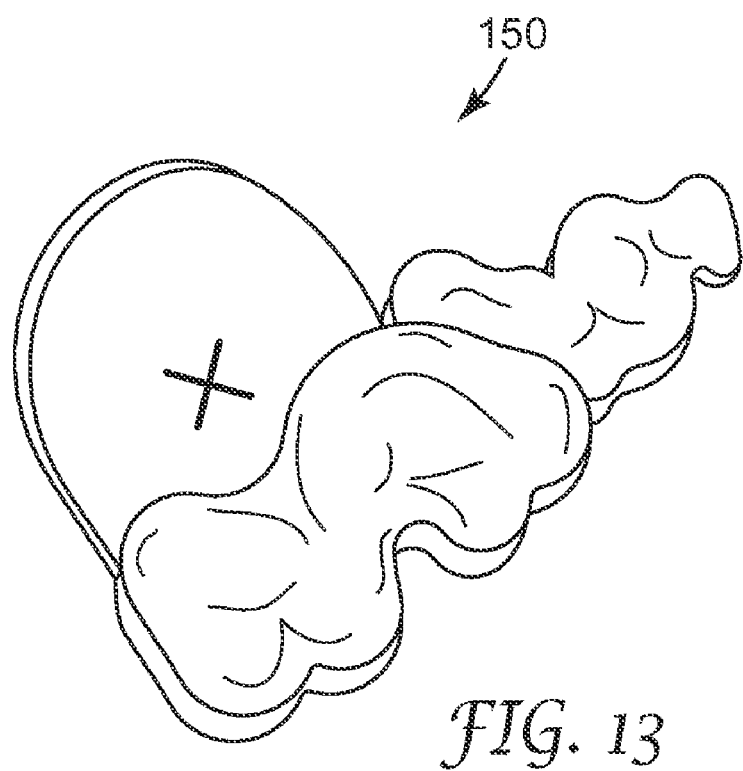
FIG. 13 is a perspective view of an alternate embodiment of a surgical guide in accordance with the invention, where the surgical guide includes a physical mark rather than an aperture to designate the temporary anchorage device implant site.
Figure 16:
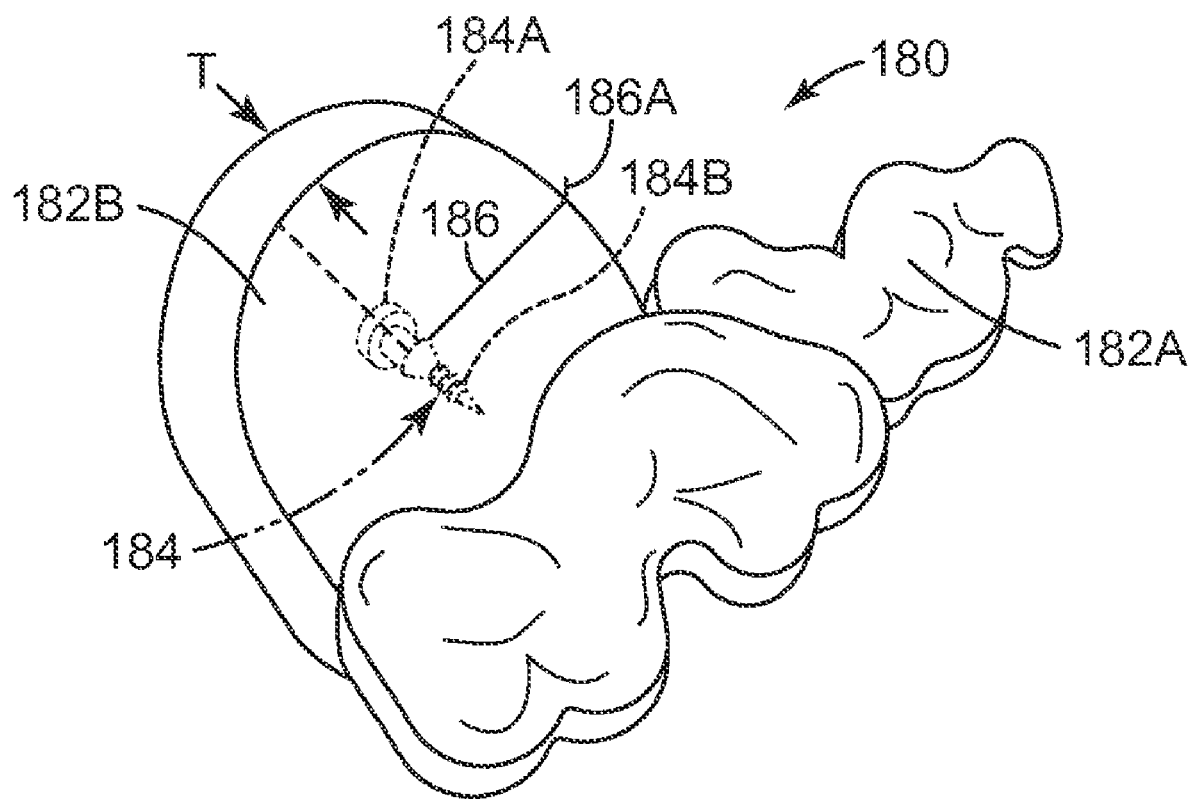
FIG. 16 is a perspective view of another embodiment of a surgical guide in accordance with the invention, where a temporary anchorage device that is embedded in a surgical guide is a marker for indicating a TAD implant site.

Surgical guide 30 may be formed to include any marker disposed on body 32 for indicating a TAD implant site and/or aligning a TAD with the TAD implant site. The marker is not limited to aperture 34, but may also include a visual indicium on body 32 (e.g., an "X" over the implant site, as shown in FIG. 13), an embedded orthodontic appliance (e.g., a steel sleeve, such as the one shown in FIG. 2B, or a TAD, as shown in FIG. 16), or other physical/structural guides, including combination markers including both a structural guide and a visual indicium. Furthermore, surgical guide 30 may include more than one marker for indicating more than one TAD implant site. In general, however, the marker is positioned on body 32 by a computer controlled instrument based on a digital representation of dental arch 10 (or at least the relevant portion of dental arch 10), thereby increasing the accuracy of the marker position. The term "accuracy," is generally used herein to refer to the extent to which the marker is configured to align with a desired TAD implant site when surgical guide 30 is properly positioned within dental arch 10. Utilizing a computer controlled instrument to position the marker and form the surgical guide may help reduce the probability of error during TAD implantation (i.e., the probability that the TAD will be implanted in a manner that damages a tooth root).

Figure 2B:
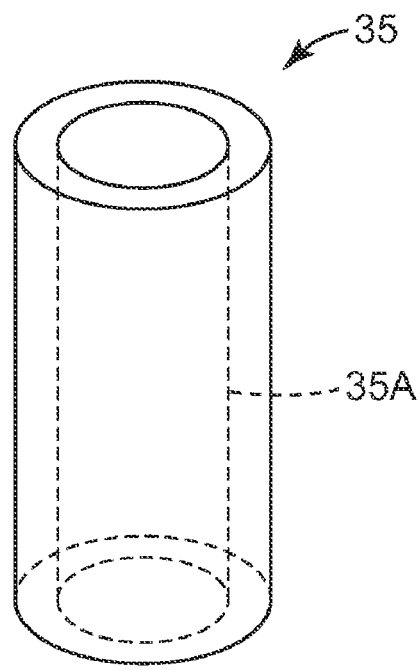
FIG. 2B is a perspective view of a hollow steel sleeve that may be disposed within an aperture of the surgical guide shown in FIG. 2A.

FIG. 2B illustrates an example of hollow steel sleeve 35. In applications in which a pilot hole is formed in jaw bone 14 prior to installing TAD 24, hollow steel sleeve 35 may be affixed to interior wall 34A of aperture 34 in body 32 of surgical guide 30 to increase the rigidity of inner wall 34A during drilling of a pilot hole for TAD 24, if TAD is not self-tapping. Hollow steel sleeve 35 may have, for example, a 2 millimeter (mm) outer diameter and a 1.3 mm inner diameter, which is defined by inner wall 35A. Inner wall 35A increases mechanical integrity of aperture 34, which helps increase accuracy when forming a pilot hole in a jaw bone. In one embodiment, steel sleeve 35 may be integrally formed with second body portion 32B of surgical guide 30. While a "steel" sleeve is referred to throughout the description of the invention, in alternate embodiments, steel sleeve 35 may be formed of any suitable material having sufficient rigidity to support a surgical bur or other instrument during the drilling of a pilot hole in a jaw bone of a patient.

Figure 3:
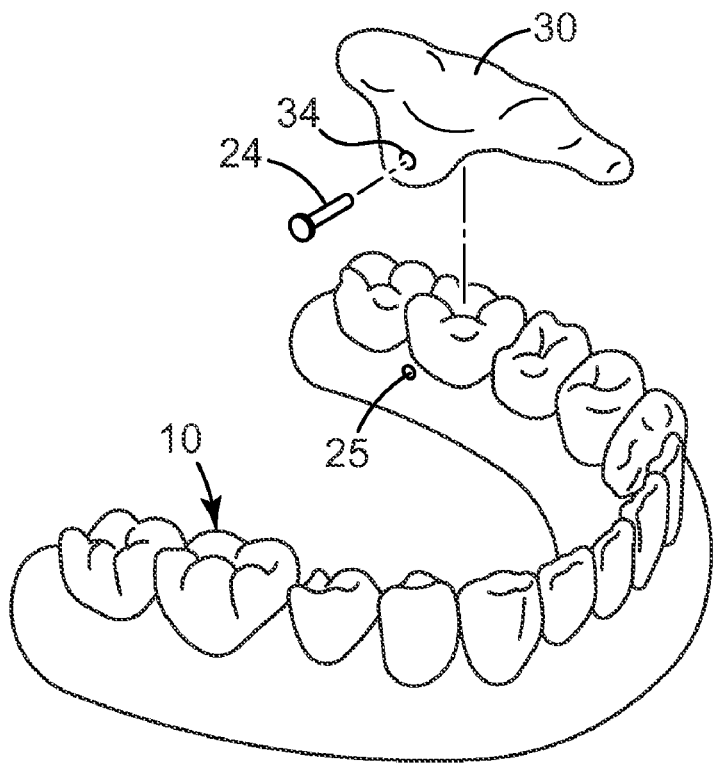
FIG. 3 is an exploded view illustrating the alignment between a dental arch of a patient, the surgical guide of FIG. 2A, and a temporary anchorage device.

FIG. 3 is an exploded view illustrating alignment between patient's dental arch 10, surgical guide 30 and TAD 24. In this arrangement, surgical guide 30 is positioned on the patient's dental arch 10 and aligned to overlay occlusal surfaces 16 of teeth 12A, 12C, and 12D. TAD 24 is aligned to be introduced into aperture 34 in second body portion 32B, and aperture 34 is aligned with implant site 25 (schematically shown).

Figure 4A:
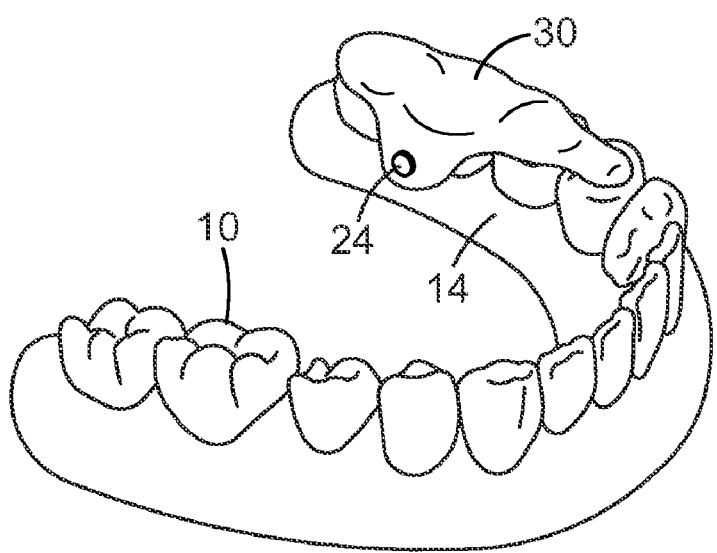
FIG. 4A is an assembled view of the exploded view of FIG. 3, where the temporary anchorage device has been implanted in a jaw bone of the dental arch.

FIG. 4A is an assembled view of the exploded view of FIG. 3, where surgical guide 30 is fit over occlusal surfaces 16 of teeth 12A, 12C, and 12D, and TAD 24 is introduced into aperture 34 in second body portion 32B, as well as implanted in jaw bone 14 of dental arch 10. As FIG. 4A illustrates, the alignment surface of first body portion 32A fits with the surface profile of the patient's dental arch 10 so that aperture 34 defined by second body portion 32A of surgical guide 30 aligns TAD 24 with a specific implant site 25. Surgical guide 30 mechanically relates the information specified by the practitioner with respect to the location and orientation for implantation of TAD 24 to the actual, physical location in dental arch 10.

Figure 4B:
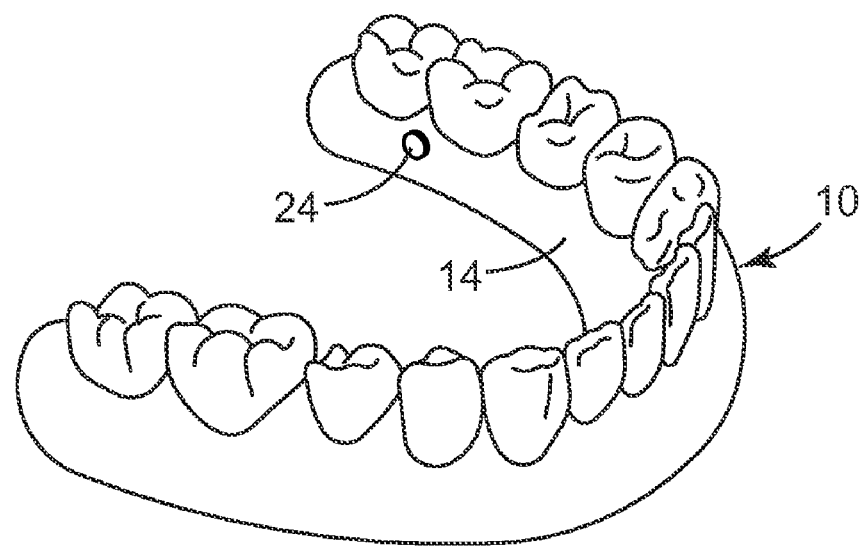
FIG. 4B illustrates the assembled view of FIG. 4A, after the surgical guide is removed from the dental arch.

FIG. 4B illustrates the assembled view of FIG. 4A, after surgical guide 30 is removed from dental arch 10. After surgical guide 30 is removed, TAD 24 remains implanted within jaw bone 14 of dental arch 10.

Figure 5:
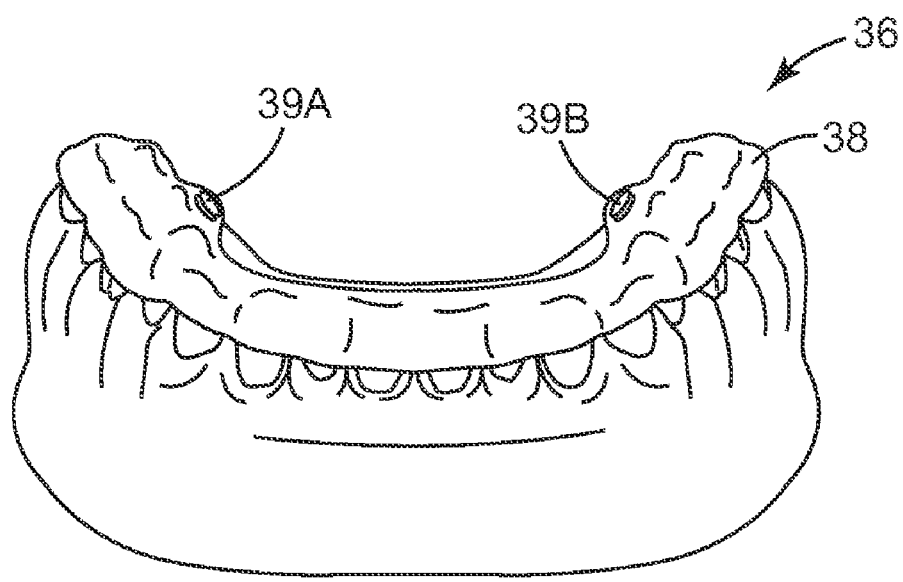
FIG. 5 is a perspective view of an alternate embodiment of a surgical guide, which is formed to overlay an occlusal surface of an entire dental arch.

FIG. 5 is a perspective view of surgical guide 36, which is an alternative design to surgical guide 30 shown in FIGS. 2A, 3 and 4A. In this example, body 38 of surgical guide 36 is formed to overlay an occlusal surface of an entire dental arch (e.g., surface 16 of dental arch 10 of FIG. 1A). That is, body 38 is formed to have an alignment surface corresponding to the surface profile of the patient's entire dental arch. Furthermore, in this example, body 38 defines two apertures 39A and 39B for receiving two TADs. In some applications, a practitioner may utilize more than one TAD, in which case surgical guide 36 may include more than one marker for indicating the multiple TAD implant sites.

Although surgical guide 30 of FIGS. 2A-4B and surgical guide 36 of FIG. 5 are formed to overlay occlusal surfaces of three teeth and an entire dental arch, respectively, the techniques may be applied to form surgical guides formed to overlay occlusal surfaces of any number of teeth of a dental arch.

Figure 6:
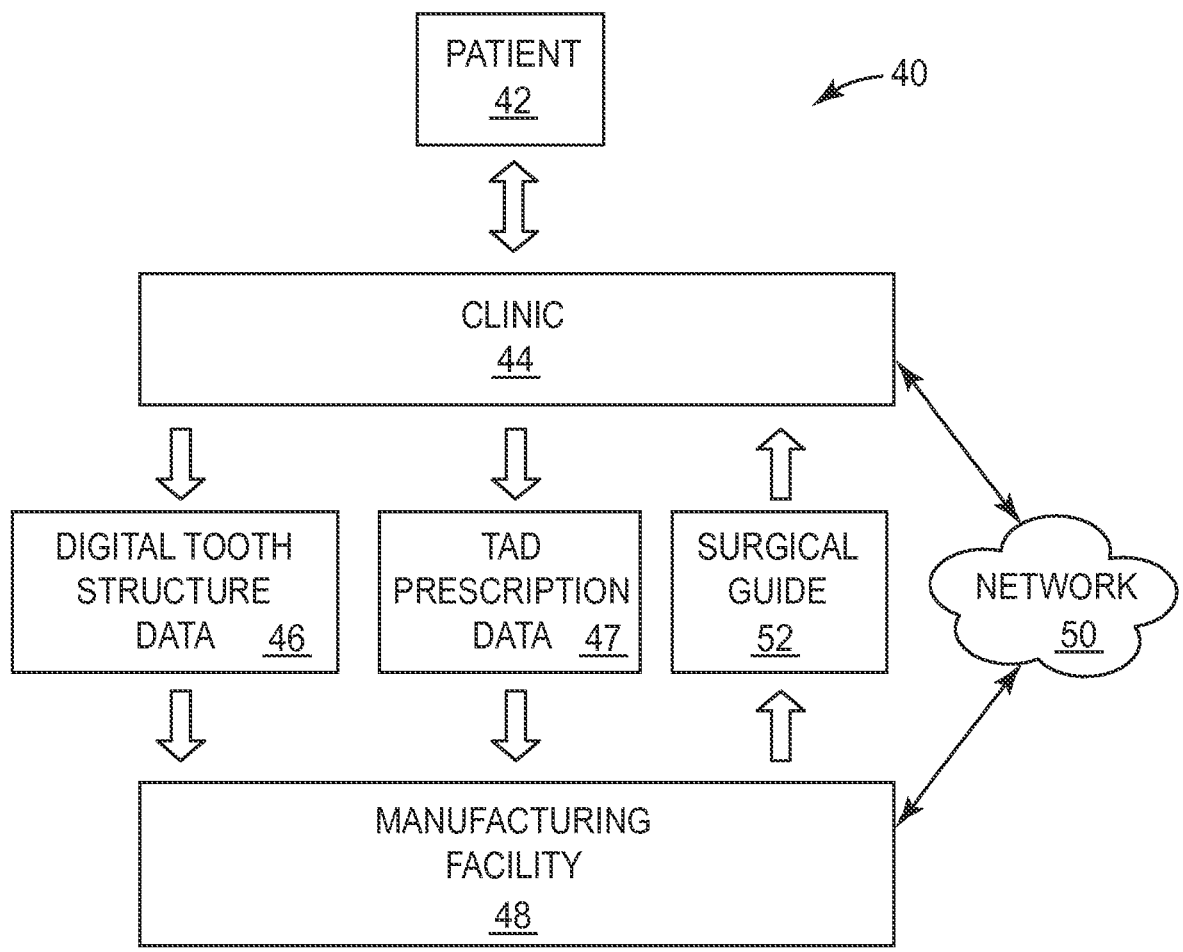
FIG. 6 is a block diagram illustrating an exemplary computer environment in which a clinic and manufacturing facility communicate information throughout a surgical guide manufacturing process.

FIG. 6 is a block diagram illustrating an exemplary computer environment 40 in which clinic 44 and manufacturing facility 48 communicate information throughout a surgical guide manufacturing process. Initially, an orthodontic practitioner of clinic 44 generates one or more radiological images of a tooth structure of patient 42 using any suitable imaging technique and generates digital tooth structure data 46 (e.g., a digital representation of patient's 42 tooth structure). For example, the practitioner may generate X-RAY images that can be digitally scanned. Alternatively, the practitioner may capture digital images of the patient tooth structure using conventional computed tomography (CT) or ultrasound instrumentation. The tooth structure may include, but is not limited to, one or more teeth of a dental arch and their respective roots, or a part of one or more teeth of the dental arch and their respective roots.

After generating digital tooth structure data 46, clinic 44 may store digital tooth structure data 46 within a patient record in a database to later associate the patient record with surgical guide 52, after manufacturing facility 48 produces surgical guide 52. Clinic 44 may, for example, update a local database having a plurality of patient records. Alternatively, clinic 44 may remotely update a central database within manufacturing facility 48 via network 50. After digital tooth structure data 46 is stored, clinic 44 electronically communicates digital tooth structure data 46 to manufacturing facility 48. Alternatively, manufacturing facility 48 may retrieve digital tooth structure data 46 from the central database within manufacturing facility 48.

Clinic 44 may also forward prescription data 47 conveying a general area for the TAD implant site or a specific TAD implant site to manufacturing facility 48. The general area within the dental arch of patient 42 for the desired TAD implant site is typically based on the orthodontic therapy program for the particular patient 42. In selecting the general area for the TAD implant site, the practitioner typically considers factors such as, but not limited to, the purpose of the TAD (e.g., the type of forces the TAD is used to create). "General area" refers to a region within the dental arch of patient 42 that is larger than a specific implant site. A general area may be, for example, between two specific teeth (e.g., the mandibular right first and second molars). A more specific TAD implant site is not typically determined until digital tooth structure data 46 is reviewed to determine the location of the tooth roots. In some embodiments, prescription data 47 may be more specific. For example, digital tooth structure data 46 may be a digital representation of the tooth structure of patient 42, and the practitioner of clinic 44 may review the digital representation and mark the desired TAD implant site, angle of insertion, and/or depth of insertion within the digital representation prior to forwarding digital tooth structure data 46 to manufacturing facility 48.

Manufacturing facility 48 utilizes digital tooth structure data 46 of patient 42 to construct surgical guide 52 for use in implanting a TAD in a jaw bone of patient 42. Some time thereafter, manufacturing facility 48 forwards surgical guide 52 to clinic 44. The orthodontic practitioner of clinic 44 may then position surgical guide 52 over the dental arch (or a portion of the dental arch) of patient 42 to correctly position the TAD within the dental arch of patient 42. Rather than relying on a visual comparison by the practitioner between a digital representation patient's 42 tooth structure (or an image, such as a radiological image) and patient's 42 actual dental arch to pinpoint a TAD implant site that does not interfere with tooth roots, surgical guide 52 physically coordinates the TAD implant site that was previously selected based on digital tooth structure data 46 to an actual location in patient 42. More specifically, as discussed previously in reference to surgical guide 30 of FIG. 2A, surgical guide 52 includes a marker that marks or otherwise conveys the location of the actual the TAD implant site to the practitioner.

A location of the marker is determined automatically by a computing device, or alternatively, by a practitioner interacting with a virtual model (e.g., digital tooth structure data 46 in the form of a digital representation or a digital representation formed from digital tooth structure data 46) of the dental structure of patient 42. Because the marker is automatically placed on (or fabricated on or within) surgical guide 52 by a prototyping device controlled by a computing device, the location of the marker on surgical guide 52 corresponds substantially accurately to the TAD implant site selected by the computer and/or practitioner. By indicating the TAD implant site within the dental arch of patient 42, surgical guide 52 helps reduce error in relating tooth root location information from digital tooth structure data 46 to the actual dental arch of patient 42.

Figure 7:
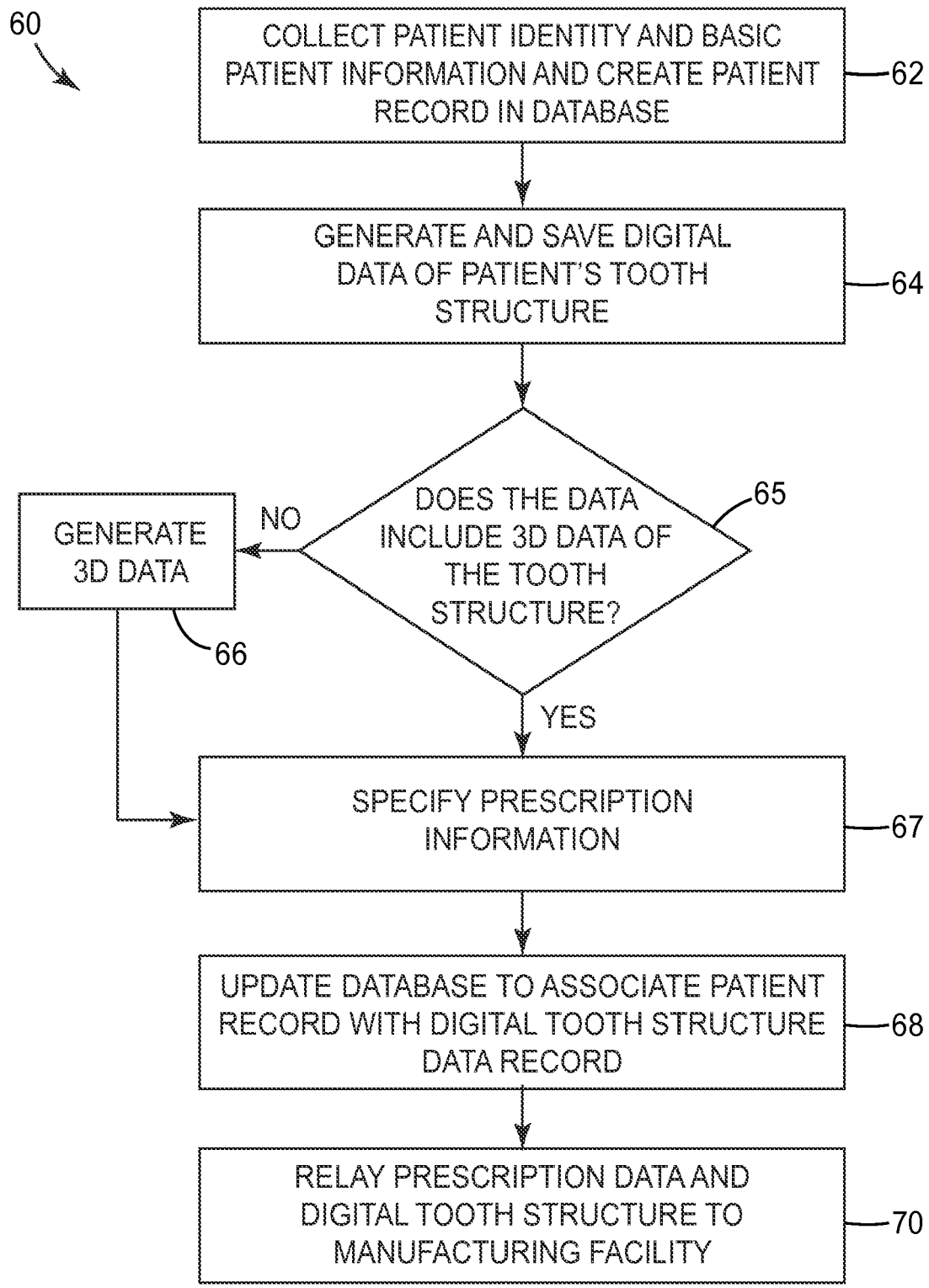
FIG. 7 is a flow diagram illustrating a process conducted at the clinic in accordance with one embodiment of the invention.

FIG. 7 is a flow diagram illustrating process 60 conducted at clinic 44 in accordance with one embodiment of the invention. Initially, a practitioner at clinic 44 collects patient identity and other information from patient 42 and creates a patient record (62). As described, the patient record may be located within clinic 44 and optionally configured to share data with a database within manufacturing facility 48. Alternatively, the patient record may be located within a database at manufacturing facility 48 that is remotely accessible to clinic 44 via network 50.

Next, digital data 46 of the tooth structure of patient 42 is generated using any suitable technique (64), to thereby create a virtual tooth structure. As previously indicated, the virtual tooth structure may include the entire dental arch of patient 42, as well as the relevant tooth roots (i.e., roots proximate to the desired TAD implant site), or a portion of the dental arch and relevant tooth roots. Digital data 46 may be comprised of a two-dimensional (2D) image and/or a three-dimensional (3D) representation of the tooth structure.

In one embodiment, 3D representations of a tooth structure are generated using a cone beam computerized tomography (CT) instrument, such as a NewTom Volumetric Scanner, which is available from Aperio Services, LLC of Sarasota, Fla. Clinic 44 stores the 3D data 46 (in the form of radiological images) generated from the CT instrument in the database located within clinic 44, or alternatively, within manufacturing facility 48. The computing system processes the digital data 46 from the CT instrument, which may be in the form of a plurality of slices, to compute a digital representation of the tooth structure that may be manipulated within the 3D modeling environment.

If 2D radiological images are used (65), the practitioner may further generate 3D digital data representing the occlusal surface of at least the relevant portion of the dental arch (66). The 3D data 46 may be produced by, for example, forming and subsequently digitally scanning a physical impression or casting of the tooth structure of patient 42. For example, a physical impression or casting of a dental arch of patient 42 may be scanned using a visible light scanner, such as a OM-3R scanner available from Laser Design, Inc. of Minneapolis, Minn. Alternatively, the practitioner may generate the 3D data 46 of the occlusal surface by use of an intra-oral scan of the dental arch of patient 42, or existing 3D tooth data. In one embodiment, the method of forming a digital scan from a casting or an impression described in U.S. Patent Application Publication No. 2007/0031790 entitled, "REGISTERING PHYSICAL AND VIRTUAL TOOTH STRUCTURES WITH PEDESTALS," and filed on Aug. 3, 2005, is used. U.S. Patent Application Publication No. 2007/0031790 is herein incorporated by reference in its entirety. As described in U.S. Patent Application Publication No. 2007/0031790, separation software may be used to identify each tooth of the virtual tooth structure and separate the teeth from each other and from the gingiva. This may be useful in allowing each tooth to independently move within the modeling environment provided b client computing device 80 and illustrate the predicted results of an orthodontic prescription.

In any case, the digital data from the 2D radiological images and the 3D data representing the surface profile of the dental arch are digitally registered within the 3D modeling environment to form a composite digital representation of a tooth structure that includes the tooth roots as well as the occlusal surfaces. The "relevant tooth roots" and "relevant portion of the dental arch" refers to the tooth roots and portion of the dental arch, respectively, proximate to the desired TAD implant site or the general area for the TAD implant site.

In one embodiment, 2D radiological images and the 3D digital data for the occlusal surface of the dental arch are registered by first attaching registration markers (e.g., fiducial markers or a pedestal having known geometry) to the tooth structure of patient 42 prior to generating both the radiological images and the 3D digital scan. Thereafter, the digital representation of the registration markers within the 2D radiological image and the 3D digital data may be aligned within a 3D modeling environment using registration techniques described in U.S. Patent Application Publication No. 2007/0031790, hereby incorporated by reference.

Alternatively, the 2D data and the 3D digital representation of the dental arch can be registered using the techniques described in U.S. Pat. No. 6,845,175, Kopelman et al, or U.S. Pat. No. 6,068,482, Snow, each of which is herein incorporated by reference in its entirety.

In another embodiment, 3D digital data of the tooth structure is generated by combining two 3D digital representations of the tooth structure. For example, a first 3D digital representation may be a relatively low resolution image of the roots obtained from a CT instrument (e.g., a NewTom Volumetric Scanner) and the second 3D digital representation may be a relatively high resolution image of the crowns of the teeth obtained from a CT scan of an impression or a visible light (e.g., laser) scan of a casting of the dental arch of the patient. The 3D digital representations may be registered using a software program that enables the 3D representations to be manipulated within a computer environment (e.g., Geomagic Studio software, available from Geomagic, Inc. of Research Triangle Park, North Carolina), or alternatively, registration techniques described in U.S. Patent Application Publication No. 2007/0031790 may be used.

Next, a computer system executing 3D modeling software renders a resultant digital representation of the tooth structure, including the occlusal surface as well as the root structure of the patient's dental arch. Modeling software provides a user interface that allows the practitioner to manipulate digital representations of the TAD in 3D space relative to the digital representation of the patient's dental arch. By interacting with the computer system, the practitioner generates prescription information, such as by selecting the desired TAD implant site (67). The practitioner may optionally control the orientation of the TAD, the implant path and depth, the number of rotations needed to thread the TAD to the desired depth, and other parameters associated with the implantation of the TAD within the patient's dental arch (67). For example, the modeling software and corresponding user interface may be adapted to allow the practitioner to implant a virtual TAD (e.g., a virtual object representing a TAD) between tooth roots in the digital representation. Alternatively, the modeling software may provide user interface mechanisms by which the practitioner can simply specify: (1) a "virtual" TAD implant site at a point along the digital representation of the dental arch, e.g., by way of a mouse or other input device, and (2) an implant angle for the TAD, e.g., by way of a drop-down menu or text-box. As used herein the "virtual" TAD implant site is a location within the digital representation of the dental arch as rendered by the modeling software, while an "actual" TAD implant site is a location within the physical tooth structure of patient 42.

Once the practitioner has virtually installed all of the desired TADs within the 3D environment, the computer system updates the database associated with the patient record to record the TAD prescription data 47 as specified by the practitioner, e.g., the selected TAD to be used, the TAD implant site, the orientation of the TAD within 3D space before and/or after implant, and/or a depth of the implant or other parameters useful in controlling the implant of the TAD within the patient's dental arch (68). Thereafter, the TAD prescription data 47 is relayed to manufacturing facility 48 in order for manufacturing facility 48 to construct one or more surgical guides, such as surgical guide 52 (70).

Although described with respect to an orthodontic practitioner located at an orthodontic clinic, one or more of the steps discussed with respect to FIG. 7 may be performed by a remote user, such as a user located at manufacturing facility 48. For example, the orthodontic practitioner may only send radiological image data and an impression or casting of the patient to manufacturing facility 48, where a user interacts with a computer system to precisely virtually implant TADs within a 3D modeling environment. Optionally, a digital representation of the TADs within the 3D modeling environment may then be transmitted to the orthodontic practitioner of clinic 44, who may review the placement and orientation of the TADs and either send back his or her approval, or modify the placement and orientation of the TADs as desired.

Figure 8:
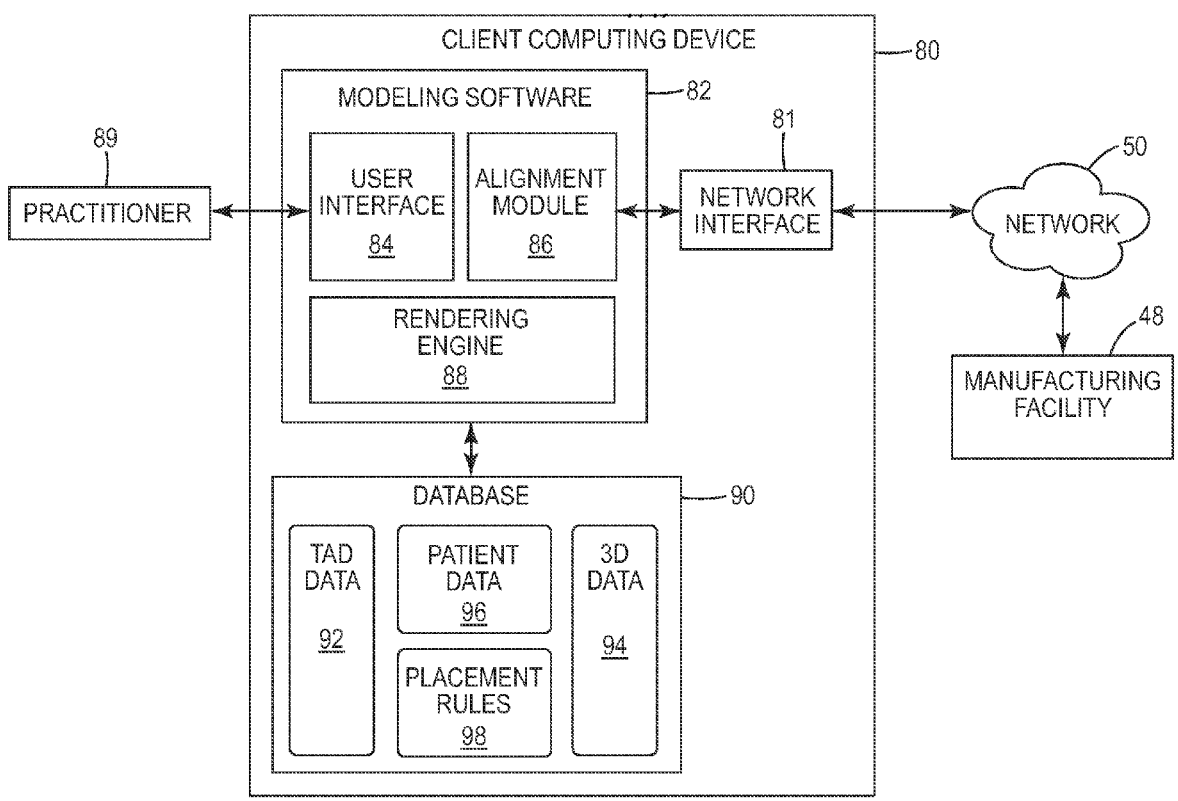
FIG. 8 is a block diagram illustrating an example embodiment of a client computing device in further detail.

FIG. 8 illustrates a block diagram illustrating an example embodiment of a client computing device 80 in further detail. In the illustrated embodiment, client computing device 80 provides an operating environment for modeling software 82. As described above, modeling software 82 presents a modeling environment for modeling and depicting the 3D representation of the teeth of patient 42. In the illustrated embodiment, modeling software 82 includes user interface 84, alignment module 86, and rendering engine 88.

User interface 84 provides a graphical user interface (GUI) that visually displays the 3D representation of patient's 42 teeth as well as 3D representations of the TADS. In addition, user interface 84 provides an interface for receiving input from practitioner 89 of clinic 44 (FIG. 6), e.g., via a keyboard and a pointing device, for manipulating the TADS and implanting the TADS within the modeled dental arch.

Modeling software 82 may be accessible to manufacturing facility 48 via network interface 81. Modeling software 82 interacts with database 90 to access a variety of data, such as TAD data 92, 3D data 94 relating to the tooth structure of patient 42, patient data 96, and TAD placement rules 98. Database 90 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS) or object relational (ORDBMS) database management system. The data may, for example, be stored within a single relational database, such as SQL Server from Microsoft Corporation. Although illustrated as local to client computer device 80, database 90 may be located remote from the client computing device and coupled to the client computing device via a public or private network, e.g., network 50.

TAD data 92 describes a set of commercially available TADs that may be selected by practitioner 89 and positioned within the 3D modeling environment. For example, TAD data 92 may store a variety of attributes for the commercially available TAD, such as dimensions, default implant locations and characteristics, suggested angles of orientation within a jaw bone, and other attributes. User interface 84 provides a menu-driven interface by which practitioner 89 selects the type of TADs for use in defining the TAD prescription data 47 for patient 42.

Patient data 96 describes a set of one or more patients, e.g., patient 42, associated with practitioner 89. For example, patient data 96 specifies general information, such as a name, birth date, and a dental history, for each patient. In addition, patient data 96 may specify a current prescription 47 specified for each of the patients, including the types of TADs and other orthodontic devices selected by practitioner 89 for use with each of the patients. In some examples, client computing device 80 includes software that enables the practitioner, patient or other observer to see on a monitor or other video output a virtual representation of the patient's teeth as they should appear at the conclusion of treatment using the selected orthodontic devices specified by the prescription 47. The software may include subprograms for selecting and placing orthodontic appliances on the virtual representation of the patient's teeth, analyzing malocclusions and/or predicting tooth movement and final positions of the teeth within the modeling environment based on the placed orthodontic appliances.

TAD placement rules 98 may specify industry-defined placement rules for commercially available TADs. In addition, placement rules 98 may include user-defined rules specified by practitioner 89 or other rules for controlling TAD placement. For example, the rules may be used to automatically compute recommended position and implant angle depending on the type of TAD and the mesial-distal location specified by practitioner. By automatically adjusting the TAD to a specified position, modeling software 80 may allow the practitioner 89 to place the TAD within the jaw so that certain placement rules are satisfied.

Rendering engine 88 accesses and renders 3D data 94 to generate the 3D view presented to practitioner 89 by user interface 84. More specifically, 3D data 94 includes information defining the 3D objects that represent each tooth (including relevant roots), jaw bone, and TAD within the 3D environment. Rendering engine 88 processes each object to render a 3D triangular mesh based on viewing perspective of practitioner 89 within the 3D environment. User interface 84 displays the rendered 3D triangular mesh to practitioner 89, and allows practitioner 89 to change viewing perspectives and manipulate objects within the 3D environment.

U.S. Patent Application Publication No. 2005/0170309 entitled, "PLANAR GUIDES TO VISUALLY AID ORTHODONTIC APPLIANCE PLACEMENT WITHIN A THREE-DIMENSIONAL (3D) ENVIRONMENT," and U.S. Patent Application Publication No. 2007/0141526, entitled, "USER INTERFACE HAVING CROSS SECTION CONTROL TOOL FOR DIGITAL ORTHODONTICS," filed on Dec. 20, 2005, describe other examples for computer systems and 3D modeling software having user interfaces that may be used with the techniques described herein, each of which are incorporated by reference in their entireties.

Figure 9:
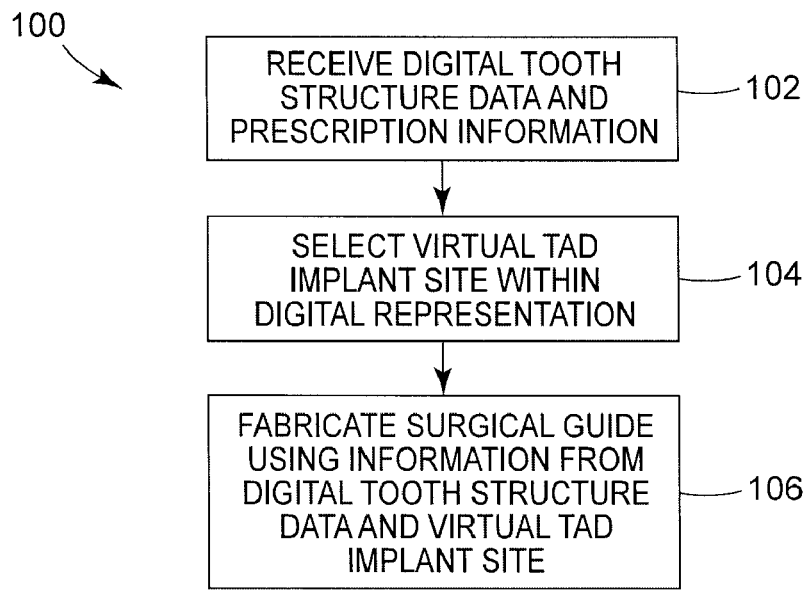
FIG. 9 is a flow diagram illustrating a process conducted at manufacturing facility in accordance with one embodiment of the invention.

FIG. 9 is a flow diagram illustrating process 100 conducted at manufacturing facility 48 in accordance with one embodiment of the invention. Manufacturing facility 48 receives digital tooth structure data 46 and prescription information 47 (102) from clinic 44. Alternatively, manufacturing facility 48 retrieves the information from a database located within or otherwise accessible by manufacturing facility 48. As discussed above, a trained user associated with manufacturing facility 48 may interact with a computerized modeling environment to virtually place and orient the desired TADs relative to the digital representation of the patient's tooth structure and generate prescription information 47, if clinic 44 has not already done so (104).

In either case, manufacturing facility 48 fabricates surgical guide 52 in accordance with the digital tooth structure data 46 and the TAD implant prescription information 47 (106). Construction of surgical guide 52 typically involves a multi-step process conducted at manufacturing facility 48. While two exemplary methods of constructing surgical guide 52 are described below, any suitable method of constructing surgical guide 52 is contemplated to be within the scope of the invention.

Figure 10:
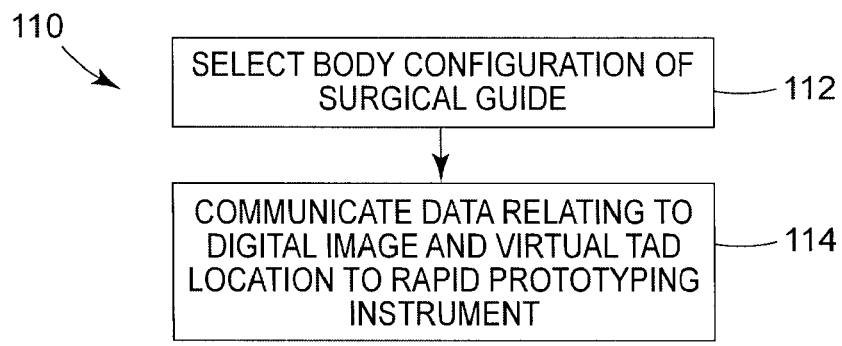
FIG. 10 is a flow diagram illustrating a process for constructing a surgical guide in accordance with one embodiment of the invention.

FIG. 10 is a flow diagram illustrating a first exemplary process 110 for constructing surgical guide 52. First, a computing device within manufacturing facility 48 (either by input from trained personnel or automatically) selects an appropriate body configuration of surgical guide 52, which is dictated by the desired portion of the dental arch that surgical guide 52 is to be formed to overlap (112). For example, it may be desirable for surgical guide 52 to fit over an occlusal surface of an entire dental arch of patient 42, or occlusal surfaces of a fewer number of teeth (e.g., a dental quadrant). Furthermore, surgical guide 52 may be constructed to cover the buccal, labial or lingual surfaces of a number of adjacent teeth, in addition to or instead of occlusal surfaces of the teeth. Alternatively, clinic 44 may instruct manufacturing facility 48 to construct surgical guide 52 having a particular body configuration.

Thereafter, the computing device of manufacturing facility 48 utilizes the 3D data 46 of the patient's dental arch, e.g., the 3D surface data related to an occlusal surface of the dental arch, as well as the TAD prescription data 47 to drive a rapid prototyping instrument to fabricate the appropriate body configuration of surgical guide 52. That is, surgical guide 52 may be formed to have an alignment surface that matches a surface profile of the occlusal surface of all or a portion of the patient's dental arch. As known in the art, a typical rapid prototyping instrument transforms a computer aided drawing (CAD) image into virtual cross sections, and then creates each cross section in physical space, one after the next until the product is finished. If necessary, manufacturing facility 48 converts the data to a format compatible with the rapid prototyping instrument (e.g., a standard stereolithographic format (STL)). Examples of rapid prototyping instruments that may be used include, but are not limited to a stereolithography instrument, selective laser sintering (SLS) instrument, and solid object printing instrument.

During the construction of surgical guide 52, the rapid prototyping instrument positions the marker, whether it be an aperture, physical mark, orthodontic appliance, or other visual indicia and/or structural guides, on (or within, as the case may be) surgical guide 52 in a position and orientation corresponding to the TAD implant prescription data 47. In this way, the marker is positioned on surgical guide 52 by a computer controlled instrument, and an alignment surface of the surgical guide is formed to easily and accurately fit over all or a portion of a surface of the patient's dental arch.

Figure 11:
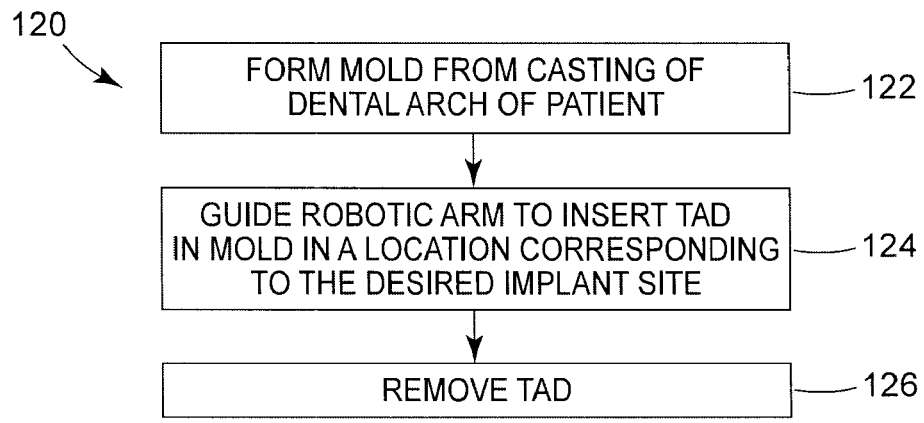
FIG. 11 is a flow diagram illustrating another process for constructing a surgical guide, in which a manufacturing facility constructs a surgical guide using a casting of at least a portion of a dental arch of a patient.

FIG. 11 is a flow diagram illustrating a second exemplary process 120 for constructing surgical guide 52, where manufacturing facility 48 constructs surgical guide 52 using a physical casting of at least a portion of the dental arch of patient 42, which clinic 44 may provide to manufacturing facility 48. Process 120 is described in further detail in reference to FIGS. 12A-12C. In general, a mold of the patient's dental arch is formed around all or a portion of the casting (122). While the mold is still positioned around the casting, manufacturing facility 48 utilizes a computer controlled robotic arm, or another computer controlled instrument, to precisely implant a TAD or a TAD place holder (i.e., an apparatus having substantially the same dimensions as a TAD) into the mold at a location corresponding to the virtual TAD implant site previously selected by clinic 44 or manufacturing facility 48. After the mold material is cured, the TAD is removed (126), such as by the robotic arm or another means. The remaining mold material defines a surgical guide that includes an aperture formed by the TAD, where the aperture marks the desired TAD implant site. In alternate embodiments, a steel sleeve or a sleeve place holder may be implanted into the mold at a location corresponding to the virtual TAD implant site.

Figure 12A:
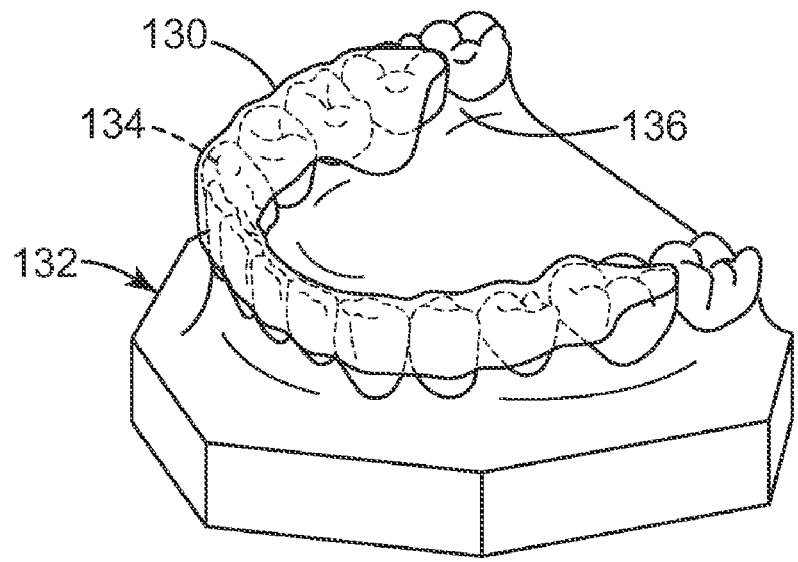
FIGS. 12A-12C illustrates the second exemplary process shown in FIG. 1.

FIG. 12A illustrates step 122 of the second exemplary process 120 shown in FIG. 11. In this example, tray 130 is placed, either manually or by flowing material in an automated fashion, around casting 132 of a dental arch of a patient. In one embodiment, tray 130 is a dental impression tray that is loaded with a quantity of a mold material (not shown). In an alternative embodiment, the tray is made according to the methods used to make indirect bonding trays such as described in pending U.S. Patent Application Publication No. 2006/0223021 entitled. "ORTHODONTIC INDIRECT BONDING APPARATUS WITH OCCLUSAL POSITIONING STOP MEMBERS" or U.S. Patent Application Publication No. 2004/0219471, entitled, "METHOD AND APPARATUS FOR INDIRECT BONDING OF ORTHODONTIC APPLIANCES" (published on Nov. 4, 2004), both of which are expressly incorporated by reference herein.

Tray 130 is adapted to extend along the entire dental arch, although as an alternative, it is possible to use a tray that extends along a fewer number of teeth, such as a dental quadrant. The mold material disposed within tray 130 is used to capture an impression of the dental arch from casting 132, so as to configure a body of a surgical guide that fits over the occlusal, buccal/labial, and/or lingual surfaces of the dental arch.

Casting 132 may be provided to manufacturing facility 48 by clinic 44, or manufacturing facility 48 may form casting 132 from a dental impression provided by clinic 44, as described in U.S. Patent Application Publication no. 2007/0031790 entitled, "REGISTERING PHYSICAL AND VIRTUAL TOOTH STRUCTURES WITH PEDESTALS." Casting 132 is a representation of the dental arch of the patient including teeth 134 (shown in phantom) and gum line 136, where a TAD is typically implanted to access the jaw bone. The term "casting" is used generally herein to refer to any type of physical model of a dental arch of a patient, for example, a replica made from plaster of Paris or from a polymeric material such as an epoxy that transmits actinic radiation. Suitable epoxy and other polymeric materials are described in U.S. Patent Application Publication No. 2004/0219473.

In this example, tray 130 is placed around casting 132 so that the mold material within tray 130 forms around at least teeth 134 and gum line 136 in the general vicinity of the desired TAD implant site.

In another embodiment, an acrylic transfer tray may be substituted for tray 130. The acrylic transfer tray may be formed by waxing around the portion of casting 132 proximate to the desired TAD implant site, or alternatively, around the entire casting 132. The area of casting 132 isolated by the wax is then wetted and coated with petroleum jelly. Cold-cure acrylic resin, or another molding material, is applied to the isolated areas to thereby form a mold of the tooth structure, including occlusal surfaces, represented by casting 132. Excess resin may be trimmed away.

Figure 12B:
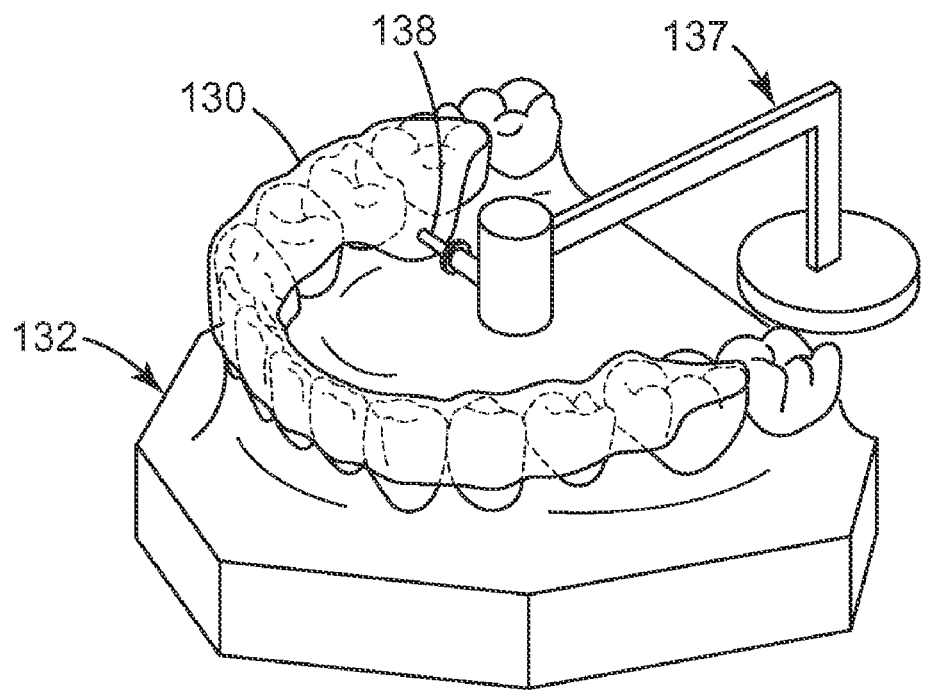

FIG. 12B illustrates step 124 of the second exemplary process 120 shown in FIG. 11. Computer controlled robotic arm 137 implants TAD 138 in tray 130 in a location corresponding to the desired TAD implant site and at an angle corresponding to the desired angle of insertion as specified by the TAD prescription data 47. Digital tooth structure data 46 may include a coordinate system that is registered to dental arch casting 132, and robotic arm 137 may be guided via coordinates to TAD 138 implant site within tray 130.

In a system of the invention, any computer controlled instrument for implanting TAD 138 in mold 130 may be used instead of robotic arm 137. For example, a computer controlled surgical bur, rather than TAD 138, may be inserted into tray 130. A computer controlled instrument is preferable so that TAD 138 is placed in mold 130 with substantial accuracy (i.e., in a location substantially corresponding to the virtual TAD implant site).

Figure 12C:
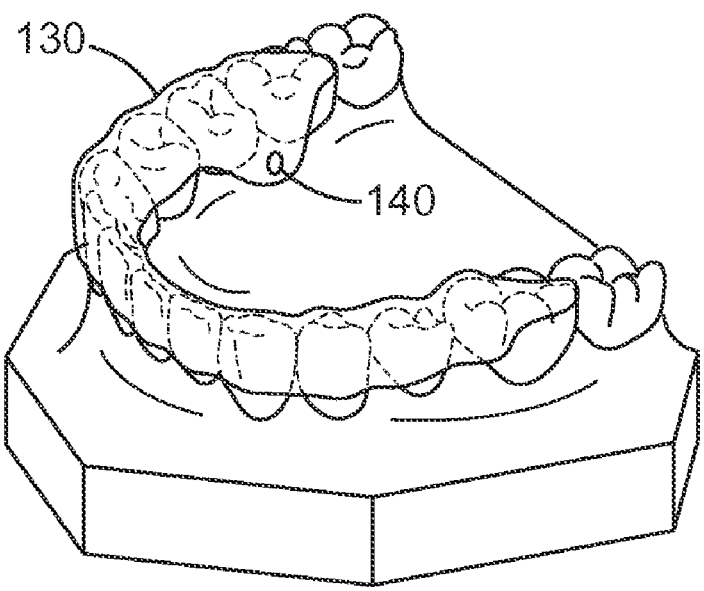

After TAD 138 is implanted within tray 130 and the mold material, the mold material is cured. Thereafter, TAD 138 may be removed from tray 130. As shown in FIG. 12C, after TAD 138 is removed from tray 130, aperture 140 remains where TAD 138 was previously implanted in tray 130. The mold material within tray 130 defines a surgical guide including an aperture that corresponds with aperture 140. If necessary, the mold material may be trimmed. In an alternate embodiment, robotic arm 137 may guide a surgical bur to create aperture 140.

FIG. 13 is a perspective view of an alternate embodiment of surgical guide 150, which is similar to surgical guide 30 of FIG. 2A except that rather than including aperture 34 to mark the TAD implant site, surgical guide 150 includes a physical marking. The "X" shown in FIG. 13 is for exemplary purposes, and any suitable marking (e.g., another shape) may be used instead of an "X." The practitioner may elect to use the TAD to self-tap an aperture on or near the marking while the surgical guide 150 is received on the dental arch, and then continue threading the TAD to advance the TAD into the dental arch. After the TAD is partially or fully implanted, the surgical guide 150 is removed from the dental arch using, for example, the frangible seams 33 illustrated in FIG. 2A. Alternatively, the practitioner may use a surgical bur to drill an aperture through the surgical guide and into the jaw bone to form a pilot hole.

Figure 14:
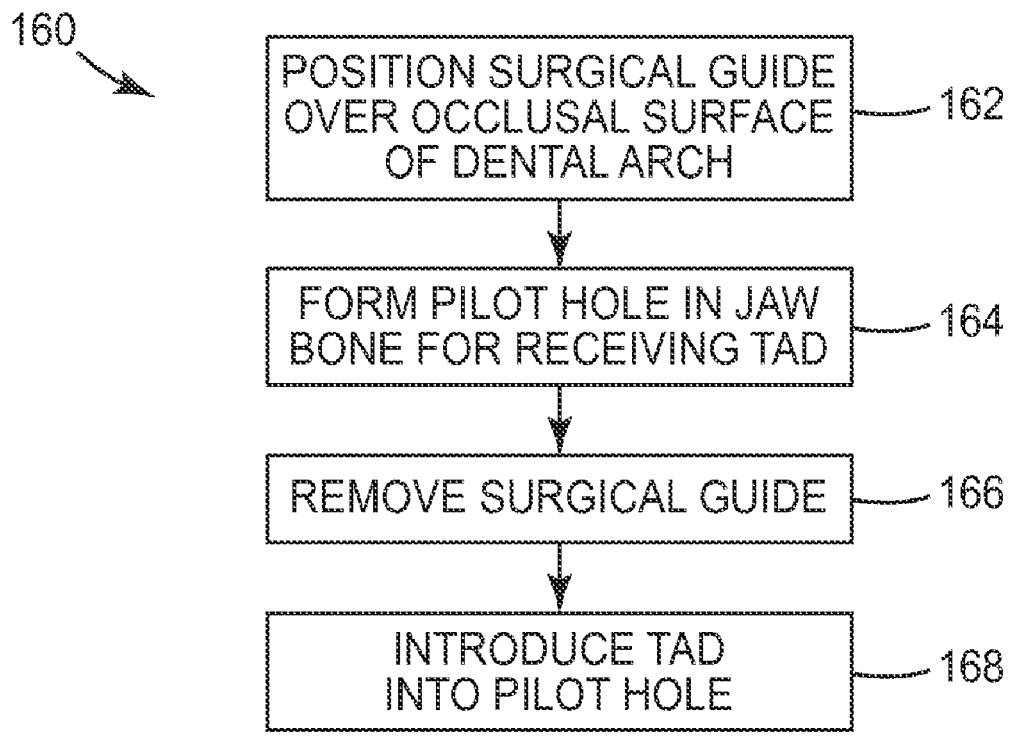
FIG. 14 is a flow diagram of a process for implanting a temporary anchorage device using a surgical guide in accordance with the invention.

FIG. 14 is a flow diagram of process 160 for implanting a TAD using a surgical guide in accordance with the invention. A surgical guide is positioned over an occlusal surface of a part of or an entire dental arch of a patient (162). When properly positioned over the occlusal surface, a marker positioned on the surgical guide indicates a TAD implant site. A hole formed to receive the TAD is formed in a jaw bone of the patient, where the hole is aligned with the marker (164). In one embodiment, the surgical guide includes a hollow steel bore disposed in an aperture, which visually indicates the TAD implant site. A surgical bur is introduced into the steel bore and into the jaw bone of the patient, thereby forming a pilot hole for the TAD (164). Thereafter, the surgical guide may be removed from the mouth of the patient (166), and a TAD may be introduced into the hole formed by the surgical bur (168).

Figure 15:
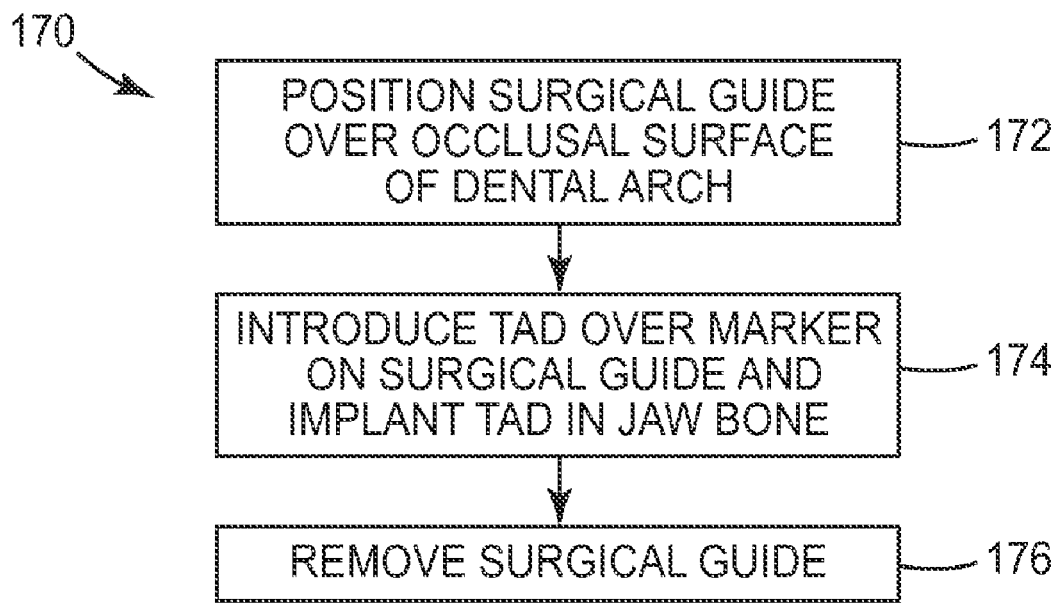
FIG. 15 is a flow diagram of another process for implanting a temporary anchorage device using a surgical guide in accordance with the invention.

FIG. 15 is a flow diagram of another process 170 for implanting a TAD in accordance with the invention. As with process 160, a surgical guide including a marker indicating a TAD implant site is positioned over an occlusal surface of a part of or an entire dental arch of a patient (172). In process 170, a self-tapping TAD is directly implanted into the jaw bone of the patient without forming a pilot hole (174). The TAD is aligned with the marker disposed on the surgical guide and advanced into the surgical guide and underlying jaw bone. After the TAD is implanted in the jaw bone, the surgical guide may be removed from the mouth of the patient (176). In one embodiment, the surgical guide is adapted to break away (e.g., with frangible seam 33 of FIG. 2A), such that the surgical guide may be removed around the implanted TAD.

FIG. 16 is a perspective view of another embodiment of surgical guide 180 in accordance with the invention. Surgical guide 180 includes first body portion 182A and second body portion 182B. Disposed within second body portion 182B is a marker that aligns a TAD with an implant site within a dental arch of a patient. In particular, TAD 184 (in phantom lines) is embedded within second body portion 182B such that when first body portion 182A is placed over an occlusal surface of the dental arch, TAD 184 is aligned with a previously selected implant site and is properly oriented with respect to a jaw bone of the patient. TAD 184 may be embedded in surgical guide 180 as surgical guide 180 is formed by a prototyping device using the surgical guide 180 fabrication methods previously described. For example, TAD 184 may be placed in surgical guide 180 by a computer controlled device (e.g., robotic arm 137 of FIG. 12B) as a prototyping device is forming first and second body portions 182A and 182B. The computer controlled device may orient TAD 184 within second body portion 182B based on prescription data (e.g., prescription data 47 of FIG. 6) that specifies, for example, an angle of insertion and/or an insertion depth for TAD 184.

A thickness T of second body portion 182B is preferably large enough to support TAD 184 in a desired orientation and support TAD 184 as TAD 184 is implanted in the jaw bone of the patient. Proximal end 184A of TAD 184 protrudes slightly from second body portion 182B so that a practitioner may easily access proximal end 184A when inserting TAD 184 into the jaw bone of the patient. A distal end 184B of TAD 184 preferably does not initially protrude past second body portion 182B so that TAD 184 does not hinder the placement of surgical guide 180 over the dental arch of the patient. However, when the practitioner screws TAD 184 into the jaw bone, TAD 184 moves toward the jaw bone, and so, distal end 184B eventually advances past second body portion 182B and into the jaw bone of the patient.

Surgical guide 180 helps streamline a TAD implantation process. Rather than positioning a surgical guide within the patient's mouth and subsequently aligning a TAD (or surgical bur) with a marker of the surgical guide in order to align the TAD with the desired implant site, surgical guide 180 combines the TAD with the surgical guide and eliminates the need to align the TAD with the marker. Thus, the practitioner may place surgical guide 180 within the patient's mouth and screw (or otherwise insert) TAD 154 into the jaw bone of the patient. After the TAD is partially or fully implanted, surgical guide 180 is removed from the dental arch. For example, a practitioner may grasp tab 186A of rip cord 186, which is also embedded in surgical guide 180 in order to cut through second body portion 182B of surgical guide 180. Alternatively, surgical guide 180 may include a frangible seam (e.g., frangible seam 33 of FIG. 2A).

Various embodiments of the invention have been described. These and other embodiments are within the scope of the following claims.

The invention claimed is:

1. A system for fabricating an orthodontic surgical guide for positioning and aligning a temporary anchorage device relative to a dental arch and a temporary anchorage implant site, wherein the temporary anchorage device facilitates orthodontic tooth movement, the system comprising:
   a computing device comprising a processor coupled to a memory and a display, the memory storing computer-readable instructions for execution by the processor, the instructions comprising
      a rendering engine for rendering a three-dimensional digital representation of at least a portion of a dental arch within a user-interactive computer environment; and
      a user interface module for manipulating a digital representation of a temporary anchorage device relative to the three-dimensional digital representation of the dental arch and specifying a virtual implant site for the temporary anchorage device; and
   a prototyping instrument in communication with the computing device and configured to fabricate an orthodontic surgical guide based on the three-dimensional representation of the dental arch, the digital representation of the temporary anchorage device, and the manipulation, in the user interactive computer environment, of the digital representation of the temporary anchorage device relative to the three-dimensional digital representation of the dental arch and the specified virtual implant site for the temporary anchorage device.

2. The system of claim 1, wherein the prototyping instrument fabricates the surgical guide to include:
   a body having an alignment surface formed to fit over at least one of a buccal, labial, lingual or occlusal surface of the portion of the dental arch; and
   a marker on the body and positioned to align with an actual implant site for the temporary anchorage device corresponding to the virtual implant site when the body of the surgical guide is positioned over the surface of the portion of the dental arch.

3. The system of claim 2, wherein the prototyping instrument fabricates the marker of the surgical guide to orient the temporary anchorage instrument within the implant site.

4. The system of claim 2, wherein the marker is an aperture defined by the body.

5. The system of claim 4, wherein the prototyping instrument fabricates the aperture to comprise an interior surface angled to receive and orient at least one of the temporary anchorage device and a surgical bur with respect to a jaw bone of a patient.

6. The system of claim 4, wherein the prototyping instrument fabricates the surgical guide to include a hollow steel sleeve disposed within the aperture.

7. The system of claim 2, wherein the marker is a visual indicium disposed on the body.

8. The system of claim 2, wherein the marker is an orthodontic appliance embedded in the body.

9. The system of claim 1, wherein the prototyping instrument is a rapid prototyping instrument.

10. The system of claim 9, wherein the rapid prototyping instrument is one of:
    a stereolithography instrument, a selective laser sintering instrument, and a solid object printing instrument.

11. The system of claim 1, wherein the prototyping instrument is an instrument comprising:
    an arm controlled by the computing device, wherein the arm is adapted to position the marker on a physical model of the portion of the dental arch.

12. The system of claim 1, wherein the prototyping instrument fabricates the surgical guide at least in part of at least one of: a polyamide nylon, a glass-filled nylon, a thermoplastic, a thermosetting resin, a polycarbonate, metal, a resin reinforced with ceramic, and a resin reinforced with glass.

13. The system of claim 2, wherein the prototyping instrument fabricates the surgical guide to comprise a plurality of visual indicia disposed on the body, wherein each marker indicates a separate implant site for a separate temporary anchorage device.

14. The system of claim 1, and further comprising a database that stores a digital representation of a type of orthodontic appliance selected for the dental arch, wherein the temporary anchorage device, in conjunction with the orthodontic appliance, is configured to facilitate orthodontic movement of at least one tooth of the dental arch.

15. The system of claim 14, wherein the computing device predicts movement of the at least one tooth based on the orthodontic appliance selected for the dental arch.

16. The system of claim 1, wherein the digital representation of the at least the portion of the dental arch rendered within the user-interactive computer environment comprises a plurality of teeth and respective roots, and wherein the teeth are independently movable within the computer environment.

17. A method of constructing an orthodontic surgical guide for positioning and aligning a temporary anchorage device relative to a dental arch and a temporary anchorage implant site, wherein the temporary anchorage device facilitates orthodontic tooth movement, the method comprising:
    generating, within a three-dimensional (3D) modeling environment, a 3D digital representation of a tooth structure of a patient;
    receiving input manipulating a digital representation of a temporary anchorage device (TAD) relative to the 3D digital representation of the tooth structure and specifying a virtual implant site for the TAD within the 3D modeling environment;

communicating data relating to the tooth structure of the patient and the specified TAD implant site to a prototyping instrument; and controlling the prototyping instrument to fabricate an orthodontic surgical guide based on the 3D digital representation of the tooth structure, the digital representation of the TAD, and the input manipulating, within the 3D modeling environment, the digital representation of the TAD relative to the 3D digital representation of the tooth structure and the specified virtual implant site for the TAD, wherein the orthodontic surgical guide includes a marker corresponding to the temporary anchorage device implant site.

18. The method of claim 17, wherein generating the digital representation of the tooth structure of the patient comprises:

imaging the tooth structure to produce a two-dimensional (2D) image of the at least one tooth and the root of the at least one tooth;

scanning at least a portion of the tooth structure to produce three-dimensional (3D) data of the at least one tooth; and registering the 2D image and 3D data to align the 2D image of the root with the at least one tooth within the 3D environment to generate a composite digital representation of the at least one tooth and the root.

19. The method of claim 18, wherein the 2D image is a radiological image.

20. The method of claim 18, wherein scanning at least a portion of the tooth structure comprises scanning at least one of a physical casting and a physical impression of the tooth structure of the patient.

21. The method of claim 18, wherein scanning at least a portion of the tooth structure comprises scanning the tooth structure of the patient with an intra-oral scanner.

22. The method of claim 18, and further comprising placing at least one registration marker on the tooth structure of the patient prior to imaging the tooth structure and prior to scanning the tooth structure, wherein registering the 2D image and the 3D data comprises defining a second registration marker in the 3D image, wherein superimposing the 2D and 3D images comprises aligning the first and second registration markers.

23. The method of claim 17, wherein generating the digital representation of the tooth structure comprises:

utilizing a CT scanner to generate three-dimensional (3D) data relating to the tooth structure; and processing the 3D data to produce the digital representation of the tooth structure able to be manipulated within the 3D modeling environment.

24. The method of claim 17, wherein the prototyping instrument is a rapid prototyping instrument.

25. The method of claim 17, wherein the prototyping instrument is adapted to construct a guide comprising a body formed to fit over at least one of a buccal, labial, lingual or occlusal surface of the at least one tooth based on the digital representation of the tooth structure within the three-dimensional modeling environment.

26. The method of claim 17, wherein the marker is an aperture defined by the body and configured to receive at least one of the temporary anchorage device and a surgical bur.

27. The method of claim 17, wherein the marker is a visual indicium disposed on the body.

28. The method of claim 17, wherein the marker is an orthodontic appliance embedded in the body.

29. The method of claim 28, wherein the orthodontic appliance is at least one of: the temporary anchorage device and a steel sleeve.

30. The method of claim 17, and further comprising:

forming a physical model of the tooth structure of the patient;

positioning a mold material around the tooth structure, wherein the prototyping instrument forms an aperture in the mold material at a location corresponding to the temporary anchorage device implant site.

31. The method of claim 30, wherein the prototyping instrument is a robotic arm.

32. The method of claim 17, wherein generating the digital representation of the tooth structure of the patient comprises:

generating a first set of three-dimensional (3D) data relating to the tooth structure of the patient, the tooth structure including the at least one tooth and the root of the at least one tooth;

generating a second set of 3D data relating to the tooth structure;

registering the first and second sets of 3D data; and processing the registered first and second sets of 3D data to produce the digital representation of the tooth structure able to be manipulated within the 3D modeling environment.

33. The method of claim 32, wherein registering the first and second sets of 3D data comprises:

defining a fiducial marker on the tooth structure prior to generating the first and second sets of 3D data; and aligning the fiducial markers on the first and second sets of 3D data.

34. The method of claim 17, wherein the temporary anchorage device is configured to facilitate orthodontic movement of the at least one tooth in conjunction with an orthodontic appliance selected for the dental arch.

35. The method of claim 34, further comprising predicting movement of the at least one tooth based on the selected orthodontic appliance.

* * * * *

UNITED STATES PATENT AND TRADEMARK OFFICE
CERTIFICATE OF CORRECTION

PATENT NO. : 7,653,455 B2 Page 1 of 1
APPLICATION NO. : 11/460640
DATED : January 26, 2010
INVENTOR(S) : David K. Cinader, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this

Twenty-third Day of November, 2010

David J. Kappos
*Director of the United States Patent and Trademark Office*